US010472638B2

(12) United States Patent
Lale et al.

(10) Patent No.: US 10,472,638 B2
(45) Date of Patent: Nov. 12, 2019

(54) SYNTHETIC MRNA LEADERS

(71) Applicant: VECTRON BIOSOLUTIONS AS, Trondheim (NO)

(72) Inventors: Rahmi Lale, Heimdal (NO); Svein Valla, Vikhammer (NO); Simone Balzer Le, Hommelvik (NO)

(73) Assignee: VECTRON BIOSOLUTIONS AS, Trondheim (NO)

( * ) Notice: Subject to any disclaimer, the term of this patent is extended or adjusted under 35 U.S.C. 154(b) by 0 days.

(21) Appl. No.: 15/300,993

(22) PCT Filed: Apr. 2, 2015

(86) PCT No.: PCT/EP2015/057337
§ 371 (c)(1),
(2) Date: Sep. 30, 2016

(87) PCT Pub. No.: WO2015/150528
PCT Pub. Date: Oct. 8, 2015

(65) Prior Publication Data
US 2017/0022509 A1    Jan. 26, 2017

(30) Foreign Application Priority Data

Apr. 3, 2014   (GB) .................................. 1406006.5

(51) Int. Cl.
| C12N 15/67 | (2006.01) |
| C12N 15/63 | (2006.01) |
| C12N 15/70 | (2006.01) |
| C12N 15/78 | (2006.01) |
| C12Q 1/6897 | (2018.01) |

(52) U.S. Cl.
CPC ............. *C12N 15/67* (2013.01); *C12N 15/63* (2013.01); *C12N 15/70* (2013.01); *C12N 15/78* (2013.01); *C12Q 1/6897* (2013.01)

(58) Field of Classification Search
None
See application file for complete search history.

(56) References Cited

U.S. PATENT DOCUMENTS

| 5,686,120 A | 11/1997 | Mertz et al. |
| 2007/0270580 A1 | 11/2007 | Mauro et al. |

FOREIGN PATENT DOCUMENTS

| WO | 98/08958 | 3/1998 |
| WO | 01/55371 | 8/2001 |
| WO | 2008/015447 | 2/2008 |
| WO | 2009/042971 | 4/2009 |

OTHER PUBLICATIONS

Archambault et al., "Translational efficiency of rpoS mRNA from *Borrelia burgdorferi*: Effects of the length and sequence of the mRNA leader region", Biomedical and Biophysical Communications, 433: 73-78 (2013).
De Amicis et al., "Improvement of the pBI121 plant expression vector by leader replacement with a sequence combining a poly(CAA) and a CT motif", Transgenic Research, 16: 731-738 (2007).
Landry et al., "Repetitive Elements in the 5' Untranslated Region of a Human Zinc-Finger Gene Modulate Transcription and Translation Efficiency", Genomics, 76(1-3): 110-116 (2001).
Borujeni et al., "Translation rate is controlled by coupled trade-offs between site accessibility, selective RNA unfolding and sliding at upstream standby sites", Nucleic Acids Research, 42(4): 2646-2659 (2014).
Na et al., "Mathematical modeling of translation initiation for the estimation of its efficiency to computationally design mRNA sequences with desired expression levels in prokaryotes", BMC Systems Biology, 4:71 (2010), 16 pages.
Salis et al., "Automated design of synthetic ribosome binding sites to control protein expression", Nature Biotechnology, 27(10):946-950 (2009), 19 pages.
Inouye et al., "Nucleotide Sequence of the promoter region of the xylDEGF operon on TOL plasmid of *Pseudomonas putida*", Gene, 29(3): 323-330 (1984).
Winther-Larsen et al., "Pm Promoter Expression Mutants and Their Use in Broad-Host-Range RK2 Plasmid Vectors", Metabolic Engineering, 2: 92-103 (2000).
Adhin et al., "Scanning Model for Translational Reinitiation in Eubacteria", Journal of Molecular Biology, 213(4): 811-818 (1990).
André et al., "Reinitiation of protein synthesis in *Escherichia coli* can be induced by mRNA cis-elements unrelated to canonical translation initiation signals", FEBS Letters, 468(1): 73-78 (2000).
Berg et al., "The expression of recombinant genes in *Escherichia coli* can be strongly stimulated at the transcript production level by mutating the DNA-region corresponding to the 5'-untranslated part of mRNA", Microbial Biotechnology, 2(3): 379-389 (2009).
United Kingdom combined Search and Examination Report, dated Jan. 22, 2015 on the priority GB application No. GB1406006.5.
Balzer et al., "A comparative analysis of the properties of regulated promoter systems commonly used for recombinant gene expression in *Escherichia coli*", Microbial Cell Factories, 12(26):1-14 (2013).

(Continued)

*Primary Examiner* — Nancy A Treptow
(74) *Attorney, Agent, or Firm* — Wenderoth, Lind & Ponack, L.L.P.

(57) ABSTRACT

The present invention provides a synthetic mRNA leader for enhancing the expression of a gene encoding a desired protein, vectors comprising said synthetic mRNA leader and methods of producing a desired gene product using said synthetic mRNA leader and vector, said method comprising expressing said gene using a synthetic mRNA leader which comprises from 5' to 3': (i) a first mRNA leader sequence element; (ii) a spacer region; and (iii) a second mRNA leader sequence element; wherein said first mRNA leader sequence element is a modified transcription-stimulating mRNA leader capable of enhancing transcription of a gene relative to an unmodified reference mRNA leader sequence and/or said second mRNA leader element is a modified translation-stimulating mRNA leader capable of enhancing the translation of a gene transcript relative to an unmodified reference mRNA leader sequence.

Figure 1:
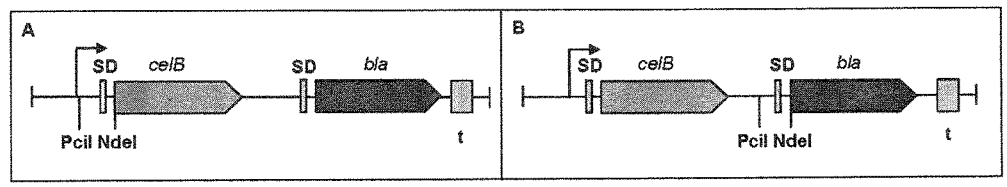

16 Claims, 8 Drawing Sheets
Specification includes a Sequence Listing.

(56) References Cited

OTHER PUBLICATIONS

Kucharova et al., "Design and Optimization of Short DNA Sequences that Can Be Used as 5' Fusion Partners for High-Level Expression of Heterologous Genes in *Escherichia coli*", Applied and Environmental Microbiology, 79(21): 6655-6664 (2013).

Berg et al., "Exploring the 5'-UTR DNA region as a target for optimizing recombinant gene expression from the strong and inducible Pm promoter in *Escherichia coli*", Journal of Biotechnology, 158: 224-230 (2012).

International Search Report and Written Opinion of the International Searching Authority, dated Jun. 11, 2015 in corresponding International Application No. PCT/EP2015/57337.

SEQUENCE LISTING

<160> NUMBER OF SEQ ID NOS: 56

<210> SEQ ID NO 1
<211> LENGTH: 35
<212> TYPE: DNA
<213> ORGANISM: Pseudomonas putida

<400> SEQUENCE: 1
aactagtaca ataataatgg agtcatgaac atatg                              35

<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2
aacggcctgc tccatgacaa                                               20

<210> SEQ ID NO 3
<211> LENGTH: 22
<212> TYPE: DNA
<213> ORGANISM: Artificial sequence
<220> FEATURE:
<223> OTHER INFORMATION: Primer

<400> SEQUENCE: 3
ctttcaccag cgtttctggg tg                                            22

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
caaggatctt accgctgttg                                               20

<210> SEQ ID NO 5
<211> LENGTH: 47
<212> TYPE: DNA
<213> ORGANISM: Artificial sequence
<220> FEATURE:
<223> OTHER INFORMATION: Primer

<400> SEQUENCE: 5
gcaggcggaa ttctaatgag gtcatgaact tatgagtatt caacatt                 47

<210> SEQ ID NO 6
<211> LENGTH: 30
<212> TYPE: DNA
<213> ORGANISM: Artificial sequence
<220> FEATURE:
<223> OTHER INFORMATION: Primer

<400> SEQUENCE: 6
ctagaggatc cccgggtacc ttttctacgg                                    30

<210> SEQ ID NO 7
<211> LENGTH: 53
<212> TYPE: DNA
<213> ORGANISM: Artificial sequence
<220> FEATURE:
<223> OTHER INFORMATION: Primer

```
<400> SEQUENCE: 7
accccttagg ctttatgcaa cagaaacaat aataatggag tcatgaactt atg          53

<210> SEQ ID NO 8
<211> LENGTH: 22
<212> TYPE: DNA
<213> ORGANISM: Artificial sequence
<220> FEATURE:
<223> OTHER INFORMATION: Primer

<400> SEQUENCE: 8
ctttcaccag cgtttctggg tg                                             22

<210> SEQ ID NO 9
<211> LENGTH: 27
<212> TYPE: DNA
<213> ORGANISM: Artificial sequence
<220> FEATURE:
<223> OTHER INFORMATION: Primer

<400> SEQUENCE: 9
cggaattcaa catgtacaat aataatg                                        27

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
agctagagga tccccgggta                                                20

<210> SEQ ID NO 11
<211> LENGTH: 86
<212> TYPE: DNA
<213> ORGANISM: Artificial sequence
<220> FEATURE:
<223> OTHER INFORMATION: Annealed oligonucleotide

<400> SEQUENCE: 11
catgtacaat aataatggag tcatgaacat atcttcatga gctccattat tattgtatat    60
gtacaataat aatggagtca tgaaca                                         86

<210> SEQ ID NO 12
<211> LENGTH: 84
<212> TYPE: DNA
<213> ORGANISM: Artificial sequence
<220> FEATURE:
<223> OTHER INFORMATION: Annealed oligonucleotide

<400> SEQUENCE: 12
tatgttcatg actccattat tattgtacat atacaataat aatggagctc atgaagatat    60
gttcatgact ccattattat tgta                                           84

<210> SEQ ID NO 13
<211> LENGTH: 29
<212> TYPE: DNA
<213> ORGANISM: Artificial sequence
<220> FEATURE:
<223> OTHER INFORMATION: Primer

<400> SEQUENCE: 13
```
gctgcatatg gtttctaaag gtgaagaag                                                29

<210> SEQ ID NO 14
<211> LENGTH: 36
<212> TYPE: DNA
<213> ORGANISM: Artificial sequence
<220> FEATURE:
<223> OTHER INFORMATION: Primer

<400> SEQUENCE: 14
gctcggatcc ttatcattta tacagttcgt ccatac                                        36

<210> SEQ ID NO 15
<211> LENGTH: 18
<212> TYPE: DNA
<213> ORGANISM: Artificial sequence
<220> FEATURE:
<223> OTHER INFORMATION: Primer

<400> SEQUENCE: 15
ccggtagcgg gacatggg                                                            18

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
caaggatctt accgctgttg                                                          20

<210> SEQ ID NO 17
<211> LENGTH: 35
<212> TYPE: DNA
<213> ORGANISM: Artificial sequence
<220> FEATURE:
<223> OTHER INFORMATION: Mutant Pm leader

<400> SEQUENCE: 17
aacatgtaca ataataatgg agtcatgaac atatg                                         35

<210> SEQ ID NO 18
<211> LENGTH: 35
<212> TYPE: DNA
<213> ORGANISM: Artificial sequence
<220> FEATURE:
<223> OTHER INFORMATION: Mutant Pm leader

<400> SEQUENCE: 18
aacatgtacc ataatacagg agttatgaac atatg                                         35

<210> SEQ ID NO 19
<211> LENGTH: 35
<212> TYPE: DNA
<213> ORGANISM: Artificial sequence
<220> FEATURE:
<223> OTHER INFORMATION: Mutant Pm Leader

<400> SEQUENCE: 19
aacatgtacc ataataacgg agtcatgaac atatg                                         35

<210> SEQ ID NO 20
<211> LENGTH: 34
<212> TYPE: DNA
<213> ORGANISM: Artificial sequence

```
<220> FEATURE:
<223> OTHER INFORMATION: Mutant Pm leader

<400> SEQUENCE: 20
aacatgtata taataatgga gaaatgaaca tatg                    34

<210> SEQ ID NO 21
<211> LENGTH: 36
<212> TYPE: DNA
<213> ORGANISM: Artificial sequence
<220> FEATURE:
<223> OTHER INFORMATION: Mutant Pm leader

<400> SEQUENCE: 21
aacatgttac catgataatg gagtcatgaa catatg                  36

<210> SEQ ID NO 22
<211> LENGTH: 35
<212> TYPE: DNA
<213> ORGANISM: Artificial sequence
<220> FEATURE:
<223> OTHER INFORMATION: Mutant Pm leader

<400> SEQUENCE: 22
aacatgtaca agtataacgg agtaatgaac atatg                   35

<210> SEQ ID NO 23
<211> LENGTH: 36
<212> TYPE: DNA
<213> ORGANISM: Artificial sequence
<220> FEATURE:
<223> OTHER INFORMATION: Mutant Pm leader

<400> SEQUENCE: 23
aacatgttac aataataacg gagtcatgta catatg                  36

<210> SEQ ID NO 24
<211> LENGTH: 35
<212> TYPE: DNA
<213> ORGANISM: Artificial sequence
<220> FEATURE:
<223> OTHER INFORMATION: Mutant Pm leader

<400> SEQUENCE: 24
aacatgtaca ataataatgg agtcatgaac atatg                   35

<210> SEQ ID NO 25
<211> LENGTH: 34
<212> TYPE: DNA
<213> ORGANISM: Artificial sequence
<220> FEATURE:
<223> OTHER INFORMATION: Mutant Pm leader

<400> SEQUENCE: 25
aacatgtagt ttaatatgga gtcattaaca tatg                    34

<210> SEQ ID NO 26
<211> LENGTH: 35
<212> TYPE: DNA
<213> ORGANISM: Artificial sequence
<220> FEATURE:
<223> OTHER INFORMATION: Mutant Pm leader

<400> SEQUENCE: 26
aacatgtact aaactaatgg agaaatgaac atatg                   35
```

```
<210> SEQ ID NO 27
<211> LENGTH: 35
<212> TYPE: DNA
<213> ORGANISM: Artificial sequence
<220> FEATURE:
<223> OTHER INFORMATION: Mutant Pm leader

<400> SEQUENCE: 27
aacatgtgca ataataatgg agtcatcaac atatg                              35

<210> SEQ ID NO 28
<211> LENGTH: 35
<212> TYPE: DNA
<213> ORGANISM: Artificial sequence
<220> FEATURE:
<223> OTHER INFORMATION: Mutant Pm leader

<400> SEQUENCE: 28
aacatgtaca acaatagtgg agtcattaac atatg                              35

<210> SEQ ID NO 29
<211> LENGTH: 35
<212> TYPE: DNA
<213> ORGANISM: Artificial sequence
<220> FEATURE:
<223> OTHER INFORMATION: Mutant Pm leader

<400> SEQUENCE: 29
aacatgtaca atcataatgg agtcataaac atatg                              35

<210> SEQ ID NO 30
<211> LENGTH: 35
<212> TYPE: DNA
<213> ORGANISM: Artificial sequence
<220> FEATURE:
<223> OTHER INFORMATION: Mutant Pm leader

<400> SEQUENCE: 30
aacatgtgca ataataatgg agtcattaac atatg                              35

<210> SEQ ID NO 31
<211> LENGTH: 35
<212> TYPE: DNA
<213> ORGANISM: Artificial sequence
<220> FEATURE:
<223> OTHER INFORMATION: Mutant Pm leader

<400> SEQUENCE: 31
aacatgtaaa aaagtaatgg agtcattaac atatg                              35

<210> SEQ ID NO 32
<211> LENGTH: 35
<212> TYPE: DNA
<213> ORGANISM: Artificial sequence
<220> FEATURE:
<223> OTHER INFORMATION: Mutant Pm leader

<400> SEQUENCE: 32
aacatgtaca ttaatatagg agtcatcaac atatg                              35

<210> SEQ ID NO 33
<211> LENGTH: 35
<212> TYPE: DNA
<213> ORGANISM: Artificial sequence
<220> FEATURE:
<223> OTHER INFORMATION: Mutant Pm leader
```

```
<400> SEQUENCE: 33
aacatgtaca ctaatagtgg agttatgaac atatg                              35

<210> SEQ ID NO 34
<211> LENGTH: 35
<212> TYPE: DNA
<213> ORGANISM: Artificial sequence
<220> FEATURE:
<223> OTHER INFORMATION: Mutant Pm leader

<400> SEQUENCE: 34
aacatgtaaa ctaataatgg agtcattaac atatg                              35

<210> SEQ ID NO 35
<211> LENGTH: 35
<212> TYPE: DNA
<213> ORGANISM: Artificial sequence
<220> FEATURE:
<223> OTHER INFORMATION: Mutant Pm leader

<400> SEQUENCE: 35
aacatgtaca atagtaatgg agtcattaac atatg                              35

<210> SEQ ID NO 36
<211> LENGTH: 35
<212> TYPE: DNA
<213> ORGANISM: Artificial sequence
<220> FEATURE:
<223> OTHER INFORMATION: Mutant Pm leader

<400> SEQUENCE: 36
aacatgtaca atgataatgg agtcataaac atatg                              35

<210> SEQ ID NO 37
<211> LENGTH: 35
<212> TYPE: DNA
<213> ORGANISM: Artificial sequence
<220> FEATURE:
<223> OTHER INFORMATION: Mutant Pm leader

<400> SEQUENCE: 37
aacatgtaaa ataatatagg agtcatcaac atatg                              35

<210> SEQ ID NO 38
<211> LENGTH: 34
<212> TYPE: DNA
<213> ORGANISM: Artificial sequence
<220> FEATURE:
<223> OTHER INFORMATION: Mutant Pm leader

<400> SEQUENCE: 38
aacatgtaaa taataatgga gtcattaaca tatg                               34

<210> SEQ ID NO 39
<211> LENGTH: 35
<212> TYPE: DNA
<213> ORGANISM: Artificial sequence
<220> FEATURE:
<223> OTHER INFORMATION: Mutant Pm leader

<400> SEQUENCE: 39
aacatgtaaa acaacaacgg agtcattaac atatg                              35

<210> SEQ ID NO 40
```

<210> SEQ ID NO 40
<211> LENGTH: 35
<212> TYPE: DNA
<213> ORGANISM: Artificial sequence
<220> FEATURE:
<223> OTHER INFORMATION: Mutant Pm leader

<400> SEQUENCE: 40
aacatgtaaa ataactatgg agtcataaac atatg    35

<210> SEQ ID NO 41
<211> LENGTH: 35
<212> TYPE: DNA
<213> ORGANISM: Artificial sequence
<220> FEATURE:
<223> OTHER INFORMATION: Mutant Pm leader

<400> SEQUENCE: 41
aacatgtgca ataataaagg agtcatcaac atatg    35

<210> SEQ ID NO 42
<211> LENGTH: 35
<212> TYPE: DNA
<213> ORGANISM: Artificial sequence
<220> FEATURE:
<223> OTHER INFORMATION: Mutant Pm leader

<400> SEQUENCE: 42
aacatgtaat aaactaaagg agttatgaac atatg    35

<210> SEQ ID NO 43
<211> LENGTH: 35
<212> TYPE: DNA
<213> ORGANISM: Artificial sequence
<220> FEATURE:
<223> OTHER INFORMATION: Mutant Pm leader

<400> SEQUENCE: 43
aacatgtact atattaatgg agagattaac atatg    35

<210> SEQ ID NO 44
<211> LENGTH: 35
<212> TYPE: DNA
<213> ORGANISM: Artificial sequence
<220> FEATURE:
<223> OTHER INFORMATION: Mutant Pm leader

<400> SEQUENCE: 44
aacatgtagt atagaaatgg agtcattaac atatg    35

<210> SEQ ID NO 45
<211> LENGTH: 35
<212> TYPE: DNA
<213> ORGANISM: Artificial sequence
<220> FEATURE:
<223> OTHER INFORMATION: Mutant Pm leader

<400> SEQUENCE: 45
aacatgtaca ttaacaaagg agtcatatac atatg    35

<210> SEQ ID NO 46
<211> LENGTH: 35
<212> TYPE: DNA
<213> ORGANISM: Artificial sequence
<220> FEATURE:
<223> OTHER INFORMATION: Mutant Pm leader

<400> SEQUENCE: 46
aacatgtact attagatagg agtcattaac atatg         35

<210> SEQ ID NO 47
<211> LENGTH: 35
<212> TYPE: DNA
<213> ORGANISM: Artificial sequence
<220> FEATURE:
<223> OTHER INFORMATION: Mutant Pm leader

<400> SEQUENCE: 47
aacatgttcg tcttcacgct aaggaggtac atatg         35

<210> SEQ ID NO 48
<211> LENGTH: 35
<212> TYPE: DNA
<213> ORGANISM: Artificial sequence
<220> FEATURE:
<223> OTHER INFORMATION: Mutant Pm leader

<400> SEQUENCE: 48
aacatgttac ttatacgagg aggttacagc atatg         35

<210> SEQ ID NO 49
<211> LENGTH: 35
<212> TYPE: DNA
<213> ORGANISM: Artificial sequence
<220> FEATURE:
<223> OTHER INFORMATION: Mutant Pm leader

<400> SEQUENCE: 49
aacatgtacc gttctttcta agcgaggttc atatg         35

<210> SEQ ID NO 50
<211> LENGTH: 52
<212> TYPE: DNA
<213> ORGANISM: Artificial sequence
<220> FEATURE:
<223> OTHER INFORMATION: Mutant Pm leader

<400> SEQUENCE: 50
gagctccatt attattgtat atgtgcatca attactaagg aggtatacta tg         52

<210> SEQ ID NO 51
<211> LENGTH: 52
<212> TYPE: DNA
<213> ORGANISM: Artificial sequence
<220> FEATURE:
<223> OTHER INFORMATION: Mutant Pm leader

<400> SEQUENCE: 51
gagctccatt attattgtat atgtgcatca ccctttaagg aggtttacta tg         52

<210> SEQ ID NO 52
<211> LENGTH: 52
<212> TYPE: DNA
<213> ORGANISM: Artificial sequence
<220> FEATURE:
<223> OTHER INFORMATION: Mutant Pm leader

<400> SEQUENCE: 52
gagctccatt attattgtat atgtaccgta cccgttaagg aggttttcta tg         52

<210> SEQ ID NO 53
<211> LENGTH: 52
<212> TYPE: DNA

```
<213> ORGANISM: Artificial sequence
<220> FEATURE:
<223> OTHER INFORMATION: Mutant Pm leader

<400> SEQUENCE: 53
gagctccatt attattgtat atgtaacaag gcagaataag gaggttcata tg          52

<210> SEQ ID NO 54
<211> LENGTH: 52
<212> TYPE: DNA
<213> ORGANISM: Artificial sequence
<220> FEATURE:
<223> OTHER INFORMATION: Mutant Pm leader

<400> SEQUENCE: 54
gagctccatt attattgtat atgtggatat acccagtaag gaggtacata tg          52

<210> SEQ ID NO 55
<211> LENGTH: 52
<212> TYPE: DNA
<213> ORGANISM: Artificial sequence
<220> FEATURE:
<223> OTHER INFORMATION: Mutant Pm leader

<400> SEQUENCE: 55
gagctccatt attattgtat atgtatataa ggattagagg aggtaatata tg          52

<210> SEQ ID NO 56
<211> LENGTH: 10
<212> TYPE: DNA
<213> ORGANISM: Artificial sequence
<220> FEATURE:
<223> OTHER INFORMATION: AU rich sequence

<400> SEQUENCE: 56
aaggagguga                                                         10
```

SYNTHETIC MRNA LEADERS

The present invention relates generally to the fields of synthetic biology, heterologous gene expression and protein production. The invention is particularly concerned with enhancing the expression (i.e. transcription and translation) of genes, particularly heterologous genes, i.e. to improve the production of a desired protein in a recombinant gene expression system. Accordingly, the invention provides a synthetic mRNA leader for enhancing the expression of a gene encoding a desired protein, said leader comprising two mRNA leader elements, namely at least one of a transcription-stimulating element and a translation-stimulating element, wherein said elements are separated by a spacer region. The invention also provides vectors comprising said synthetic mRNA leader and methods of producing a desired gene product using said synthetic mRNA leader and vector. Further methods of the invention include methods of identifying said transcription-stimulating and translation-stimulating elements and optimizing translation-stimulating elements. In particular, the transcription-stimulating and translation-stimulating elements may be produced by mutating mRNA leader sequences.

The mechanisms underlying gene expression have been extensively studied in many organisms due to their fundamental importance for the understanding of cell function and for application in biotechnology. It is particularly important to have an understanding of the mechanisms affecting expression in recombinant protein production to establish which factors may affect the level of expression.

It is well known in the art that protein production occurs through two basic steps, namely transcription (to form mRNA from the DNA template) and translation (of the mRNA to form a protein). Transcription can be delineated into three phases—initiation, elongation and termination. Hence, initiation of transcription begins with the binding of RNA polymerase to the promoter and ends with the conversion of the DNA and enzyme into an elongation complex. In between these steps, the polymerase and promoter undergo a series of alterations that include promoter binding and activation and RNA chain initiation and promoter escape. Promoter binding has been extensively studied in both prokaryotes and eukaryotes, where the interactions between RNA polymerase with general transcription factors, promoter specific factors and DNA sequences of the recognition regions of promoters have been investigated. The promoter binding-activation phase leads to the formation of the open promoter complex which interacts with NTP substrates to initiate transcription. Short RNA transcripts can then usually form which can be elongated if the polymerase escapes the promoter and moves downstream.

Promoter escape is the last stage of transcription initiation where the RNA polymerase should leave the promoter region and advance to downstream regions. If the RNA polymerase has a poor ability to escape the promoter, then abortive transcripts may be produced. Hence, the initial transcribing complexes carry out repeated initiation and abortive release without promoter escape. In vitro studies have shown that changes in the promoter recognition region (from −60 to −1) may affect the abortive rate, probability and size of abortive transcripts.

Hence, changes in the promoter and its recognition region have been studied in the art. Particularly, since the promoter plays an important part in the control of transcription, mutations in the promoter region have been previously studied to determine their effect on gene expression. For example, mutations in the Pm promoter at the −10 region which lies upstream of the transcriptional start site may facilitate gene-independent enhancement or reduction of expression and/or improved regulatory control of recombinant gene expression (WO 00/68375).

Translation of mRNA into protein occurs by interaction of mRNA with a ribosome. At least three different types of interactions between the mRNA and ribosome are known to occur. The protein moiety of the 30S subunit has an affinity for RNA, enabling binding in a non-sequence specific manner. Secondly, the 3' end of 16S rRNA interacts with a short stretch of complementary nucleotides, known as the Shine-Dalgarno sequence, located upstream from most natural initiation codons in the 5' untranslated region. Finally, the anti-codon of fMet-tRNA pairs with the initiation codon.

It is well known that in bacteria the efficiency of ribosome binding is primarily determined by the secondary structure of the mRNA in the translational initiation region (the mRNA leader or 5' untranslated region (5'UTR)—these terms are used interchangeably throughout the description). Mutations which have been made to hairpin structures in this region have been shown to effect the expression by translation. Further, alterations to the Shine-Dalgarno sequence in the 5' untranslated region have also been suggested to affect translation. In fact, extending the Shine-Dalgarno sequence in the mRNA leader has been shown to reduce translation, although this inhibitory effect could be counteracted by introducing into the leader AU-rich sequences which serve as targets for ribosomal protein 51, upstream of the Shine-Dalgarno sequence. Mutations upstream of the ribosome binding site may also affect translational efficiency. Mutations made at or upstream of the Shine-Dalgarno sequence may vary the stability of mRNA by alteration of its secondary structure or removal of a portion of the Shine-Dalgarno sequence.

Therefore, it is well known in the art that mutations which affect the secondary structure of the mRNA leader or the Shine-Dalgarno sequence may affect translation.

It has also been shown that it is possible to generate 5'-UTR variants (i.e. mutants) which stimulate expression of recombinant genes both at the transcriptional and translational level relative to the unmutated (i.e. wild-type) 5'UTR (WO2008/015447). It was concluded from these findings that mutant 5'-UTR sequences that enhance expression of recombinant genes might represent a compromise between transcriptional and translational stimulation, and that it may not be possible to identify a 5'-UTR sequence optimized for both these processes.

Accordingly, in the context of production systems for desired proteins (i.e. the expression of recombinant or heterologous genes) the factors (at the transcriptional and translational control levels) primarily thought to be important or determinative in the level or rate of expression achieved are the promoter and 5'UTR, at the transcriptional level. At the translational level, the 5'UTR is also known to have an effect on gene expression.

In the context of protein production systems in bacteria, transcription and translation are coupled, wherein there is a physical link between transcript formation and transcript turnover (translation and mRNA degradation). The translation rate is also likely to affect the transcription rate which indirectly affects mRNA stability. Since initiation is the rate limiting step during translation, which the 5'-UTR is involved in, its sequence contributes to the overall gene expression outcome. In other words, this region is one crucial contributor to the maintenance of a balance between transcription, transcript stability and translation.

In the fields of metabolic engineering and synthetic biology, it is desirable to be able to predictably control the levels of expression of a heterologous gene in order to maximize protein output. However, to achieve maximal expression at the protein level, an ideal 5'-UTR should be enhanced or optimized with respect to all functionalities and this is not straightforward because transcription and translation functionalities overlap in the sequence. Whilst there are several in silico tools available for design of synthetic 5'-UTR sequences for efficient translation initiation (Na et al., (2010) BMC Syst Biol 4: 71 and Salis et al., (2009) Nat Biotechnol 27: 946-950), because of its sequence proximity both to the promoter and coding region it has proven difficult to design optimal 5'-UTR sequences solely based on translational properties.

Surprisingly, the present inventors have now found that it is possible to enhance, e.g. optimize, expression of a desired gene (i.e. to produce a desired protein) in a recombinant gene expression system (more particularly a desired heterologous gene in a recombinant host, that is a host organism engineered to express said heterologous gene) by designing new synthetic 5'-UTR sequences that are extended in length relative to a typical wild-type 5'UTR sequence, such as the Pm 5'UTR, to provide enough space for the physical separation of an element that has been designed to enhance transcription and an element that has been designed to enhance translation. The combination of two 5'-UTR DNA elements with distinct characteristics at the transcriptional and translational levels results in a significant and completely unexpected synergistic effect on expression, relative to either element alone. Hence, the invention concerns the production and use of a synthetic mRNA leader, which may be viewed as a dual mRNA leader or dual 5'UTR, i.e. comprising two mRNA leader elements. Furthermore, the inventors have demonstrated that it is possible to optimize the translation element of the synthetic 5'UTR in silico predictably to enhance production of a protein, which partially eliminates the need for screening. Moreover, successful combinations of elements that have been designed to enhance transcription and elements that have been enhanced for translation can be predicted to occur with high frequency. The inventors have also demonstrated that the use of the synthetic 5'UTR to enhance expression of a desired, e.g. heterologous, gene is capable of functioning in multiple organisms. Hence, the invention may be seen to provide an enhanced expression system with universal utility.

The inventors utilized the Pm/xylS promoter system from a TOL plasmid to exemplify the invention, but it will be evident that the invention is not limited to this system. In brief, the inventors mutated the Pm 5'UTR to generate genetic elements for use in a synthetic 5'UTR comprising a first sequence proximal to the promoter that is enhanced, e.g. optimized, with respect to transcription and a second sequence distal to the promoter (i.e. downstream or 3' to the first sequence) that is enhanced, e.g. optimized, for translation. To identify the mutated sequences, new functional tools were needed. Accordingly, the inventors also designed two types of synthetic operons. A first operon is useful for screening and/or identifying sequences that primarily affect transcription; the second operon is useful for screening and/or identifying of mutants that affect translation.

Accordingly, in one aspect the invention can be seen to provide a method of enhancing expression of a desired gene product in a recombinant gene expression system, said method comprising expressing said gene using a synthetic mRNA leader which comprises from 5' to 3':

(i) a first mRNA leader sequence element;
(ii) a spacer region; and
(iii) a second mRNA leader sequence element;
wherein said first mRNA leader sequence element is a modified transcription-stimulating mRNA leader capable of enhancing transcription of a gene relative to an unmodified reference mRNA leader sequence and/or said second mRNA leader element is a modified translation-stimulating mRNA leader capable of enhancing the translation of a gene transcript relative to an unmodified reference mRNA leader sequence.

In a further aspect, the invention provides a synthetic mRNA leader sequence capable of enhancing expression of a desired gene product in a recombinant gene expression system, which comprises from 5' to 3':

(i) a first mRNA leader sequence element;
(ii) a spacer region; and
(iii) a second mRNA leader sequence element;
wherein said first mRNA leader sequence element is a modified transcription-stimulating mRNA leader capable of enhancing transcription of a gene relative to an unmodified reference mRNA leader sequence and/or said second mRNA leader element is a modified translation-stimulating mRNA leader capable of enhancing the translation of a gene transcript relative to an unmodified reference mRNA leader sequence.

In another aspect, the invention provides a method of identifying a transcription-stimulating mRNA leader (e.g. a leader sequence or element), said method comprising:

(a) providing a test nucleotide sequence corresponding to a test mRNA leader;
(b) inserting the nucleotide sequence of (a) into a polycistronic expression cassette comprising from 5' to 3':
(i) a first gene, being a desired gene and/or reporter gene that can be efficiently transcribed and translated;
(ii) a spacer region; and
(iii) a second gene, being a reporter gene,
wherein said nucleotide sequence is inserted upstream of said first gene and wherein said spacer region is suitable for ensuring that the translation of the said second gene is independent of the translation of said first gene,
(c) expressing said polycistronic cassette, preferably in a host cell;
(d) determining the level of expression of said second gene; and
(e) selecting a transcription-stimulating mRNA leader by selecting a nucleotide sequence which increases expression of said second gene relative to an unmodified reference mRNA leader when used as a leader upstream of said first gene in the polycistronic expression cassette, wherein said increased expression indicates enhanced transcription of said first gene and hence that said test nucleotide sequence corresponds to a mRNA leader sequence element capable of stimulating transcription.

In a still further aspect, the invention provides a method of identifying a translation-stimulating mRNA leader (e.g. a leader sequence or element), said method comprising:

(a) providing a test nucleotide sequence corresponding to a test mRNA leader;
(b) inserting the nucleotide sequence of (a) into a polycistronic expression cassette comprising from 5' to 3':
(i) a first gene, being a reporter gene that can be efficiently transcribed and translated;
(ii) a spacer region; and
(iii) a second gene, being a desired gene and/or a reporter gene, wherein said nucleotide sequence is inserted downstream of said spacer region and upstream of said second gene and wherein said spacer region is suitable for ensuring that the translation of said second gene is independent of the translation of said first gene, (c) expressing said polycistronic cassette, preferably in a host cell;

(d) determining the level of expression of said second gene; and (e) selecting a translation-stimulating mRNA leader by selecting a nucleotide sequence which increases expression of said second gene relative to an unmodified reference mRNA leader when used as a leader upstream of said second gene in the polycistronic expression cassette, wherein said increased expression indicates enhanced translation of said second gene and hence that said test nucleotide sequence corresponds to a mRNA leader sequence element capable of stimulating translation.

In another embodiment, the invention provides a vector for the selection or identification of:

(A) a transcription-stimulating mRNA leader (e.g. a leader sequence or element) for use in a synthetic mRNA leader of the invention, said vector comprising:

(i) a promoter, (ii) a polycistronic expression cassette comprising from 5' to 3':

(a) a first gene, being a desired gene and/or reporter gene that can be efficiently transcribed and translated;

(b) a spacer region; and (c) a second gene, being a reporter gene, and (iii) an insertion site for a DNA region corresponding to said transcription-stimulating mRNA leader upstream of said first gene, wherein said spacer region is suitable for ensuring that the translation of the said second gene is independent of the translation of said first gene, or (B) a translation-stimulating mRNA leader (e.g. a leader sequence or element) for use in a synthetic mRNA leader of the invention, said vector comprising:

(i) a promoter, (ii) a polycistronic expression cassette comprising from 5' to 3':

(a) a first gene, being a reporter gene that can be efficiently transcribed and translated;

(b) a spacer region; and (c) a second gene, being a desired gene and/or a reporter gene, and (iii) an insertion site for a DNA region corresponding to said translation-stimulating mRNA leader upstream of said second gene, wherein said spacer region is suitable for ensuring that the translation of the said second gene is independent of the translation of said first gene.

The invention also provides the use of a vector of the invention for screening of transcription-stimulating mRNA leaders or translation-stimulating mRNA leaders for use in a synthetic mRNA leader of the invention, which results in enhanced expression of a desired gene.

In a still further embodiment, the invention provides a method of optimizing a synthetic mRNA leader of the invention for expression of a desired (e.g. heterologous) gene product, said method comprising:

(a) determining the translational initiation rate (TIR) for a translational-stimulating mRNA leader (e.g. a leader sequence or element) in combination with a desired gene using the ribosome binding site (RBS) calculator;

(b) applying the forward engineering function of the RBS calculator to increase the TIR value;

(c) selecting a translation-stimulating mRNA leader with a higher TIR than the initial translational-stimulating mRNA leader; and (d)(i) modifying the sequence of the translation-stimulating mRNA leader of the synthetic mRNA leader to correspond to the sequence of the optimized translation-stimulating mRNA leader from (c); or (ii) inserting the optimized translation-stimulating mRNA leader from (c) into a nucleic acid molecule to produce an optimized synthetic mRNA leader, wherein the translation-stimulating leader (e.g. element) is inserted upstream of said desired gene and downstream of a transcription-stimulating mRNA leader.

Enhancing expression refers to increasing or improving, and in particular embodiments optimizing or maximizing, expression (transcription and translation) relative to a reference or control level of expression, e.g. a modified mRNA leader element enhances transcription and/or translation relative to an unmodified (reference) mRNA leader. Thus an increased amount of the desired gene product may be produced. More particularly, an increased amount of protein is produced in the expression system. (The term "protein" is used broadly herein to include any protein, polypeptide or peptide encoded by the desired gene.)

Effectively, the present invention combines two mRNA leaders, at least one of which has been modified to enhance transcription (namely to provide a transcription-stimulating mRNA leader element) or to enhance translation (namely to provide a translation-stimulating mRNA leader element), preferably both. The two leaders are incorporated into the synthetic leader which can accordingly be seen to comprise two mRNA leader "elements". A mRNA leader element thus simply refers to a nucleic acid molecule or nucleotide sequence, or a part thereof, that is capable of functioning as a mRNA leader. A mRNA leader element may be a transcription-stimulating element, i.e. a transcription-stimulating mRNA leader, or a translation-stimulating element, i.e. a transcription-stimulating mRNA leader. In particular, a mRNA leader element is a modified transcription- or translation-stimulating mRNA leader.

The term "modified" is used herein to denote that a mRNA leader sequence has been selected, designed or altered (e.g. mutated), in particular so as to enhance (improve or increase etc.) transcription or translation. In other words, the ability of the leader to enhance transcription or translation is improved or increased, or an ability or effect of the leader to enhance transcription or translation is conferred by the "modification". Alternatively expressed, the leader is "adapted" to enhance transcription or translation respectively.

An unmodified reference mRNA leader sequence may be a native or wild-type mRNA leader, e.g. a mRNA leader sequence derived from a gene, operon and/or expression system of a cell, virus or organism, such as a leader from a desired gene, Pm mRNA leader, a lac mRNA leader, a PT7φ10 mRNA leader or a Ptrc mRNA leader. In other embodiments, an unmodified reference leader may contain sequence variation(s) over the wild-type or native sequence, but such variations have not been introduced for the purpose of enhancing transcription or translation and in particular do not act to enhance transcription or translation. In some embodiments, an unmodified reference mRNA leader may be an artificial mRNA leader, e.g. a designed mRNA leader. For instance, an artificial mRNA leader may be designed de novo based on the structural features that are known to be required for a nucleotide sequence to function as a leader, e.g. a Shine-Dalgarno sequence, and/or a randomly generated sequence that is a capable of functioning as an mRNA leader. Such an artificial mRNA leader may also be a modified leader according to the invention, for example an artificial leader may be designed or selected to have transcription- or translation-stimulating properties.

A transcription-stimulating mRNA leader or leader element (alternatively a transcription-inducing element, transcription-facilitating element or a transcription-assisting element) refers to a nucleotide sequence that, when used as a mRNA leader (i.e. in the context of a gene expression system comprising a promoter, mRNA leader and polypeptide coding sequence) results in a level of gene transcription which is increased as compared to, or relative to, the level of gene transcription without the transcription-stimulating element, and more particularly as compared to, or relative to an unmodified reference sequence, i.e. an unmodified mRNA leader sequence. In particular, an increase in the level of gene transcription may be an increase in the rate of transcription compared to, or relative to, an unmodified mRNA leader sequence. However, it will be clear from the discussion below that a transcription-stimulating element is not limited to increasing transcription, i.e. it may also result in an increase in translation (or the rate of translation), e.g. relative to, compared to, an unmodified mRNA leader. In other words, in some embodiments, a transcription-stimulating element is not exclusively a transcription-stimulating element. Alternatively viewed, in some embodiments, a transcription-stimulating element primarily results in increased transcription as defined above.

A translation-stimulating mRNA leader or leader element (alternatively a translation-inducing element, translation-facilitating element or a translation-assisting element) refers to a nucleotide sequence that, when used as a mRNA leader (i.e. in the context of a gene expression system comprising a promoter, mRNA leader and polypeptide coding sequence) results in a level of gene transcript translation (i.e. protein production or expression) which is increased as compared to, or relative to, the level of gene transcript translation without the translation-stimulating element, and more particularly as compared to, or relative to, an unmodified reference sequence, i.e. an unmodified mRNA leader sequence. In particular, an increase in the level of gene transcript translation may be an increase in the rate of translation compared to, or relative to, an unmodified mRNA leader sequence. Although this is generally found not to be the case, it is not precluded that a translation-stimulating leader/leader element may also have an effect in enhancing transcription. Thus analogously to the above, a translation-stimulating leader/leader element may primarily result in increased translation as defined above.

Thus, in some embodiments a mRNA leader element, e.g. a transcription- or translation-stimulating element is a modified mRNA leader sequence that has been adapted, e.g. mutated, designed or selected, as compared to, or relative to, an unmodified mRNA leader. Thus, a modified mRNA leader sequence may be a mutated, designed or selected mRNA leader that, when used as a mRNA leader results in a level of gene transcription or gene transcript translation which is increased as compared to, or relative to, the level of gene transcription or gene transcript translation without the modified mRNA leader sequence, and more particularly as compared to, or relative to an unmodified mRNA leader. In particular, a modified mRNA leader may be a mutated leader, i.e. a sequence in which one or more mutations are introduced. Accordingly, an unmodified reference mRNA leader may be viewed as an unmutated mRNA leader, i.e. a native or artificial (e.g. designed) mRNA leader in the absence of the (introduced) mutations. Such an "unmutated" mRNA leader which is used as the starting point for the mutations introduced according to the present invention may in some embodiments be a "wild-type" leader. Suitable examples of native or wild-type mRNA leaders include a leader from a desired gene, a Pm mRNA leader, a lac mRNA leader, a PT7φ10 mRNA leader or a Ptrc mRNA leader.

In some embodiments, a transcription-stimulating element may also result in an increased level or rate of translation as defined above.

In some embodiments, an mRNA leader element, e.g. a transcription- and/or translation-stimulating element, may have a higher transcription initiation rate (TIR) than a reference nucleotide sequence, e.g. an unmodified or unmutated mRNA leader. The TIR may be determined using the ribosome binding site (RBS) calculator described in more detail below. In particular, the mRNA leader element, e.g. transcription- and/or translation-stimulating element, may have a higher TIR than a reference sequence for a particular gene, e.g. a desired gene and/or heterologous gene.

Thus, in some embodiments the transcription-stimulating element may have a TIR that is at least 1.1 fold higher than an appropriate reference sequence, e.g. the corresponding unmutated mRNA leader, such as at least 1.2, 1.3, 1.4, 1.5, 1.6, 1.7, 1.8, 1.9, 2.0, 2.2 or 2.5 fold. Alternatively, viewed the TIR of the transcription-stimulating element may be increased by at least 10, 20, 30, 40, 50, 60, 70, 80, 90, 100, 120, 150 or 200% relative to an appropriate reference sequence. Similarly, in some embodiments the translation-stimulating element may have a TIR that is at least 1.1 fold higher than an appropriate reference sequence, e.g. the corresponding unmutated mRNA leader, such as at least 5.0, 6.0, 7.0, 8.0, 9.0, 10.0, 11.0, 12.0, 13.0 or 14.0 fold. Alternatively, viewed the TIR of the translation-stimulating element may be increased by at least 100, 200, 300, 400, 500, 600, 700, 800, 900, 1000, 1100, 1200, 1300 or 1400% relative to an appropriate reference sequence. In some embodiments, the translation-stimulating element may be optimized, such that the TIR may be increased by at least 15 fold relative to the initial translation-stimulating element. For example, the TIR may be increased by at least 20, 50, 100, 200, 500, 1000, 2000, 3000, 5000, 10000, 20000, 50000, 100000 fold.

Thus, in some embodiments, the mRNA leader elements, e.g. transcription- and/or translation-stimulating elements may be artificial leader sequences. An artificial leader may be adapted or derived from a naturally occurring leader, e.g. it may be a leader which has been modified or mutated over the native form, i.e. is a derivative or variant of a naturally occurring leader (e.g. a sequence modified derivative or variant) but which does not contain the mutations according to the present invention (i.e. does not contain the transcription- or translation-enhancing mutations which are introduced). In particular, any modification or mutation which the artificial leader may contain relative to the native leader as it occurs in nature does not affect expression, and particularly transcription. In some embodiments, an artificial leader sequence may be a designed nucleic acid sequence or a randomly generated nucleic acid sequence, i.e. a sequence that is not derived from known native or wild-type mRNA leader. In preferred embodiments, artificial mRNA leader elements, e.g. transcription- and/or translation-stimulating elements, comprise sequences with a low folding energy, i.e. sequences that do not fold readily to form secondary structures. In some embodiments, the mRNA leader elements, e.g. transcription- and/or translation-stimulating elements, contain a Shine-Dalgarno region as defined below.

The mRNA leader elements, e.g. transcription- and/or translation-stimulating elements, may each consist of nucleotide sequences of 10-150 nucleotides, such as 11-140, 12-130, 13-120, 14-110 or 15-100 nucleotides. Thus, the mRNA leader elements, e.g. transcription- and/or translation-stimulating elements, may comprise 15, 20, 25, 30, 35, 40, 45, 50 nucleotides, such as 16-90, 17-80, 18-70, 19-60, 20-50, e.g. 20-45, 20-40 or 20-35 nucleotides.

A spacer region refers to a part or region of a nucleic acid molecule that separates two other parts or elements of said nucleic acid molecule, e.g. a part of a nucleic acid molecule that separates two functional elements of said nucleic acid molecule. A spacer region may be any size or length suitable to achieve its function, which can be determined by routine analysis.

Thus, in the context of a synthetic mRNA leader of the invention, the spacer region or element functions to separate the mRNA leader elements, e.g. the transcription-stimulating element from the translation-stimulating element, e.g. to prevent unwanted interactions or interference between the elements and/or to allow modularity and flexibility for later modifications to the elements, e.g. replacement of one or more elements or further mutation of said elements. Thus, in some embodiments the spacer region may comprise at least 4 nucleotides, such as at least 5, 6, 7, 8, 9, 10, 11, 12, 13, 14, 15, 16, 17, 18, 19, 20, 25, 30, 40, 50, 100 or 200 nucleotides. For instance, the spacer region may comprise between 4-200, 5-150, 6-125, 7-100, 8-90, 9-80 or 10-70 nucleotides.

In the context of the polycistronic operon or expression cassette used in the methods of the invention, the spacer region or element functions to ensure that translation of each gene in the operon is independent. In other words, the spacer region must be of sufficient size to ensure that translation of the second gene in the operon (e.g. the desired gene and/or reporter gene) is only possible through de novo initiation (as opposed to translational read-through from the first gene). Thus, in some embodiments the spacer region may comprise at least 10 nucleotides, such as at least 10, 11, 12, 13, 14, 15, 16, 17, 18, 19, 20, 25, 30, 40, 50, 100, 200, 300, 400, 500 or 1000 nucleotides. For instance, the spacer region may comprise between 10-1000, 15-900, 20-800, 30-700, 40-600, 50-500 or 60-400 nucleotides.

A synthetic mRNA leader refers to any sequence that is capable of functioning as a mRNA leader that is not a native mRNA leader, i.e. comprising elements (sequences) of a leader that allow the transcription of the gene to which it is associated and translation of the resultant transcript, wherein said elements are not found together in nature. In particular, a synthetic mRNA leader of the invention comprises two mRNA leader elements, e.g. a transcription-stimulating element and a translation-stimulating element, wherein said elements are separated by a spacer region. Accordingly, a synthetic mRNA leader may comprise mRNA leader elements, e.g. transcription- and translation-stimulating elements, that are derived from different sources, or mRNA leader elements, e.g. transcription- and translation-stimulating leader sequences, derived from the same source, but arranged in a manner different than that found in nature.

A synthetic mRNA leader (e.g. a dual mRNA leader) that enhances expression of a desired, e.g. heterologous, gene means said synthetic mRNA leader enhances transcription and translation (i.e. gene expression) to a level or rate which is increased as compared to, or relative to, the level or rate of gene expression without the synthetic mRNA leader, more particularly as compared to, or relative to a mRNA leader element, e.g. a transcription-stimulating element or translation-stimulating element, as defined above, when used alone. Thus, in other words enhanced gene expression is gene expression which is increased when using a synthetic mRNA leader of the invention, or put more specifically a synthetic mRNA leader of the invention in which the mRNA leader elements, e.g. transcription- and/or translation-stimulating elements, are enhanced, as compared, or relative, to a corresponding synthetic mRNA leader in which the mRNA leader elements, e.g. transcription- and translation-stimulating elements, are wild-type mRNA leaders, preferably wherein the mRNA leader elements, e.g. transcription- and translation-stimulating elements, consist of the same mRNA leader. Thus, the expression attainable with the recombinant gene expression system according to the present invention, e.g. with a promoter and the synthetic mRNA leader, may be compared with the expression obtained from the same expression system, but using mRNA leader elements, e.g. transcription- and translation-stimulating elements, that are unmodified leaders rather than modified leaders, e.g. adapted, designed or selected artificial or mutant leaders. Hence, an "unmodified" or "unmutated" expression system uses the same gene and promoter as the system where enhanced expression is seen, but the mRNA leader elements, e.g. transcription- and translation-stimulating elements, are not modified, e.g. adapted, designed, selected or mutated. The mRNA leader used in an "unmodified" or "unmutated" expression system (i.e. reference expression system) is therefore the unmutated or unmodified mRNA leader, i.e. the "starting" leader, where no manipulations have been carried out to enhance expression. The unmodified leader is the leader before modification (before adaptation, mutation etc.) i.e. in embodiments where the mRNA leader elements, e.g. transcription- and translation-stimulating elements, are derived from native or wild-type mRNA leaders, the unmodified leader is the leader into which the mutations may be introduced. It may be seen as a "wild-type", "native", "source" or "origin" or "starting" leader or a leader which is the substrate or target for the mutations (more particularly, references herein to the leader include, or refer to, the DNA corresponding to the mRNA leader).

An mRNA leader, e.g. a synthetic mRNA leader of the invention, typically is located 3' to (i.e. downstream of) the promoter and 5' to (i.e. upstream of) a gene in a gene expression system or operon. In a polycistronic operon, at least one mRNA leader (e.g. the first mRNA leader in the operon) is located as defined above, wherein other mRNA leaders may be located between genes, e.g. downstream of a first gene and upstream of a second gene in said operon, downstream of a second gene and upstream of a third gene in said operon and so on.

According to the invention, gene expression is enhanced by using a combination of mRNA leader elements, e.g. a transcription-stimulating element and a translation-stimulating element, wherein said elements are separated by a spacer region. However, it will be evident from the examples that the mRNA leader elements are capable of enhancing transcription and/or translation independently of each other. Thus, to achieve the synergistic increase in gene expression (i.e. transcription and translation) it is not necessary that both elements are capable enhancing transcription and translation, respectively, relative to an unmodified reference mRNA leader. In some embodiments, the transcription-stimulating element is capable of enhancing transcription of a heterologous gene relative to an unmodified mRNA leader. In preferred embodiments, at least the translation-stimulating element is capable of enhancing translation of a desired, e.g. heterologous, gene transcript relative to an unmodified mRNA leader. In particularly preferred embodiments, the transcription-stimulating element is capable of enhancing transcription of a desired, e.g. heterologous, gene relative to an unmodified mRNA leader and the translation-stimulating element is capable of enhancing translation of a desired, e.g. heterologous, gene transcript relative to an unmodified mRNA leader.

Thus, there may be an enhancement of both gene transcription and translation, even if only one of the elements in the synthetic mRNA leader is enhanced relative to an unmodified mRNA leader. Thus, in some embodiments, the mRNA elements result in a synergistic (e.g. greater than a cumulative, cooperative or combined) increase in the level and/or rate of expression relative to an unmodified mRNA leader. The synergistic effect may be seen when only one of the mRNA elements is enhanced relative to an unmodified leader. In preferred embodiment, the synergistic effect occurs when both of the mRNA elements are enhanced relative to an unmodified leader, i.e. when the synthetic mRNA leader contains both transcription- and translation-stimulating elements.

Whilst not wishing to be bound by theory it is hypothesized that the transcription-stimulating element results in enhanced transcription and the translation-stimulating element results in enhanced translation. For instance, when the transcription- and translation-stimulating elements are mutated mRNA leaders, some mutations in the leaders may enhance translation in addition to the transcription-enhancing mutation(s) and/or the mutation which enhances transcription may itself enhance translation indirectly, e.g. by an increased number of transcripts being produced and/or directly e.g. by also affecting ribosome binding, or otherwise enhancing the process of translation. Notwithstanding this, an important aspect of the present invention is the overall enhancement of transcription and translation (e.g. a synergistic enhancement or cumulative, cooperative or combined enhancement) caused by coupling the transcription- and translation-stimulating elements in a synthetic mRNA leader, which result in an increase in the amount of protein produced.

An enhancement of translation can either occur as a result of an enhancement of transcription or can be independent of transcription. Hence, an enhancement of translation which is independent of transcription could result from, for example, more efficient ribosome binding and the actual process of translation, rather than as a result of more transcripts being present due to enhanced transcription. Such an enhancement of translation which is independent of transcription could be due to an alteration of the secondary structure of the mRNA leader sequence. An enhancement of translation which is a result of enhanced transcription is therefore due to, for example the increased number of transcripts being available for translation. Gene expression in the present invention may be enhanced by an enhancement of transcription and an enhancement of translation which is a direct result of the enhancement of transcription. However, enhancement of gene expression by an enhancement of transcription and an enhancement of translation, which is both independent of transcription and as a direct result of transcription, is also encompassed. It is possible, for example, that the transcription-stimulating element allows enhanced transcription (and enhanced translation may occur as a result of this) and that the translation-stimulating element improves the secondary structure of the synthetic mRNA leader to provide enhanced (transcription independent) translation. Alternatively, it is possible that transcription-stimulating element allows enhanced transcription (and enhanced translation which is a direct result of the enhanced transcription) and also enhanced translation which is independent of the transcriptional effect, e.g. by improved ribosome binding. It is preferred in this instance that enhanced translation, which is independent of transcription, caused by the transcription-stimulating element is not due to an improved secondary structure.

In some embodiments, at least 10%, 20%, 30%, 40%, 50%, 60%, 70%, 80% or 90% of the enhanced gene expression may be caused as a result of enhancement of transcription, e.g. as a result of the production of an increased number of transcripts and/or an increase in the rate of transcription. In some embodiments, at least 10%, 20%, 30%, 40%, 50%, 60%, 70%, 80% or 90% of the enhanced gene expression may be as a result of enhanced translation, e.g. as a result of improved translation initiation and/or an increase in the rate of translation initiation. Whilst it may be possible that significant or substantially all of the enhancement of gene expression may be due to enhancement of transcription or translation, it is generally observed that enhancement of transcription is combined with an enhancement of translation. The synergistic enhanced gene expression effect of the elements of the synthetic mRNA leader of the invention (i.e. enhanced protein production) is thought to be attributable to a combination of both transcriptional and translational effects (i.e. elements that enhance both transcription and translation, e.g. the rate of transcription and translation).

Transcription of a heterologous gene can be enhanced by up to, for example, 46 fold or more when using a synthetic mRNA leader of the invention compared to an unmutated or unmodified leader as defined above. Translation a heterologous gene transcript can be enhanced by up to, for example, 170 fold or more when using a synthetic mRNA leader of the invention compared to an unmutated or unmodified leader as defined above. However, it will be appreciated that this may vary significantly, depending upon the precise system used, and what the starting point is, for example relative to a system using a leader where only low levels of expression are obtained, a much higher enhancement in the amount of protein product obtained may be achievable.

Thus, an increase of transcription or the rate of transcription (for example determined by the amount of transcript produced) of 50- or 60-fold or more may be attainable. In other systems or under other conditions the increase may be less. By way of example only, transcription of the gene (or the rate of transcription) may be enhanced by at least 60, 50, 40, 30, 27, 25, 24, 23, 22, 21, 20, 17, 15, 13, 10, 8, 6, 4 or 2 fold in a system using a synthetic mRNA leader of the invention compared to expression using the corresponding unmutated or unmodified mRNA leader as defined above. Alternatively viewed, the minimum level of enhancement which can be seen is 1.1 fold, wherein transcription or the rate of transcription can be enhanced by at least 1.2, 1.3, 1.4, 1.5, 1.6, 1.7, 1.8 or 1.9 fold. Transcription or the rate of transcription can be increased by at least 10, 20, 30, 40, 50, 60, 70, 80, 90, or 100%. Other levels include at least 200, 300, 400 or 500%. The level or rate of enhanced transcription of the heterologous gene can be measured by any convenient method known in the art. For example, transcription can be determined by measuring transcript accumulation, e.g. using Northern blotting, array technology or real-time PCR.

In some embodiments, increased transcription may be measured or detected by measuring protein accumulation or protein activity as discussed below. In other words, an increase in expression, as measured by protein accumulation or activity, may indicate (i.e. be indicative of) increased or enhanced transcription, e.g. the level or rate of transcription.

Similarly, an increase of translation or the rate of translation (for example determined by the amount of protein produced) of 180- or 200-fold or more may be attainable. In other systems or under other conditions the increase may be less. By way of example only, translation of the gene (or the rate of translation) may be enhanced by at least 200, 180, 160, 140, 120, 100, 80, 60, 50, 40, 30, 27, 25, 24, 23, 22, 21, 20, 17, 15, 13, 10, 8, 6, 4 or 2 fold in a system using a synthetic mRNA leader of the invention compared to expression using the corresponding unmutated or wild-type mRNA leader as defined above. Alternatively viewed, the minimum level of enhancement which can be seen is 1.1 fold, wherein translation or the rate of translation can be enhanced by at least 1.2, 1.3, 1.4, 1.5, 1.6, 1.7, 1.8 or 1.9 fold. Translation or the rate of translation can be increased by at least 10, 20, 30, 40, 50, 60, 70, 80, 90, or 100%. Other levels include at least 200, 300, 400, 500, 1000, 5000 or 10000%. The level or rate of enhanced translation of the heterologous gene transcript can be measured by any convenient method known in the art. For example, translation can be determined by measuring protein accumulation, protein activity (i.e. the activity of the expressed protein), wherein the levels of protein activity obtained using the synthetic mRNA leader as opposed to the unmodified mRNA leader are increased or enhanced. Alternatively, the amount of protein produced can be measured to determine the level of enhanced expression (i.e. transcription and/or translation), for example by Western blotting or other antibody detection systems, or indeed by any method of assessing or quantifying protein. Many such methods are known in the art.

In order to identify transcription- and/or translation-stimulating elements, such as mRNA leader mutants which stimulate or enhance transcription and/or translation (i.e. expression), the desired protein product can be expressed with a tag or as a fusion protein, e.g. a his tag or other suitable detection means, which can allow the measurement of gene expression using one assay for all different protein products. Particularly preferred as a method of identifying transcription- and/or translation-stimulating elements is to express the protein from a polycistronic expression cassette system (i.e. operon) defined below, where the desired gene is translationally coupled to a reporter gene. Thus, in some embodiments, the methods of the invention utilize a gene which comprises a desired gene translationally coupled to a reporter gene, i.e. to generate a fusion protein. Alternatively viewed, the polycistronic operon may comprise a gene encoding a desired protein translationally coupled to a reporter gene. Preferably the gene encoding the desired protein is provided upstream (i.e. 5') of the reporter gene. Particularly, a reporter gene is selected whose expression level correlates with the expression level of the desired gene. The levels of expression of the desired gene can therefore be assessed directly or an indirect indication of its expression level may be obtained by measuring the expression level of the reporter gene which has been used. Thus, in some embodiments the level of expression of the desired gene can be assessed directly, e.g. the reporter gene may be the desired gene or the desired gene may have a readily detectable activity akin to a reporter gene.

Reporter gene expression can be determined by the activity of the protein encoded by the reporter gene. For example, if GFP was used, levels of fluorescence obtained would correlate to the level of gene expression of the desired gene product. Attractive reporters to use are those whose activity or presence it is possible to quantify or assess (e.g. semi-quantitatively) efficiently or readily, particularly those which result in growth or growth inhibition or cell death, as such reporters can be readily assessed by determining cell (e.g. colony) growth or non-growth. Antibiotic resistance markers fall into this category, e.g. bla encoding β-lactamase. B/a is particularly attractive as resistance correlates well to expression level. Reporters based on activity of the gene product may also be used, e.g. reporter genes encoding an enzyme which may produce or be involved in the production of a detectable product or in a detectable reaction. An example of such a reporter is the luc gene encoding luciferase. Such "activity-based" reporters however require individual clones to be assayed. Particularly preferred reporter genes which can be used in the polycistronic operon described above (and which can be translationally coupled to the gene expressing the desired gene product) are beta-lactamase (bla), firefly luciferase (luc) and mCherry (a red fluorescent protein derived from *Discosoma* sp).

Increased expression of the desired gene and/or reporter gene may be used to indicate enhanced transcription and/or translation, depending on the method. Thus, in methods of identifying a transcription-stimulating mRNA leader (e.g. a leader sequence or element), the level of expression of the desired and/or reporter gene (e.g. as detected by protein accumulation or activity) may be used to indicate an increase in transcription. Similarly, in methods of identifying a translation-stimulating mRNA leader (e.g. a leader sequence or element), the level of expression of the desired and/or reporter gene (e.g. as detected by protein accumulation or activity) may be used to indicate an increase in translation.

A polycistronic operon or expression cassette refers to a region of a nucleic acid that can be transcribed to produce a single mRNA that carries several open reading frames (ORFs), each of which is translated independently into a polypeptide. A dicistronic or bicistronic operon or expression cassette refers to a nucleic acid that encodes an mRNA that can be transcribed to produce a single mRNA that encodes only two proteins. In a preferred embodiment, the polycistronic operon of the invention is a bicistronic operon.

A Shine-Dalgarno sequence may be present upstream of each ORF or gene in the polycistronic operon. In particular, a Shine-Dalgarno sequence is present upstream of the gene that is not proximal to the (test) nucleotide sequence (that may be a mRNA leader element, e.g. a transcription- or translation-stimulating element) inserted into the operon in the methods of the invention.

The first gene in the polycistronic operon of the invention must be a gene that can be efficiently transcribed and translated, i.e. such that it does not inhibit, constrain, restrict or impede the rate of transcription of the operon, i.e. it does not introduce any undesired restriction on the rate of transcription. Examples of genes that can be efficiently transcribed and translated are known in the art. For instance, the celB gene, which encodes phosphoglucomutase, is transcribed and translated efficiently and may be used as the first gene in the polycistronic operon of the invention. Any suitable gene may be used in the polycistronic operon and, in some embodiments, the first gene used in the operon may have been modified to optimize its transcription and/or translation. Methods of optimizing transcription and/or translation are known in the art, e.g. modification of sequences to that may form secondary structures and/or codon optimization.

A method of the invention is for the production of a desired gene product by the expression of the gene encoding the desired product (e.g. by the expression of a heterologous gene encoding the desired protein product). The present invention is thus concerned with methods of recombinant gene expression. As noted above, methods of recombinant gene expression are well known in the art and have been used industrially or commercially for the production of proteins. A variety of different expression systems are known and may be used to express the gene according to the present invention, i.e. as the basis for the present invention. At its most basic, an expression system includes a promoter for expression of the desired gene and the gene it is desired to express, or a site for insertion of the desired gene, such that it may be expressed under the control of the promoter. According to the present invention, the expression system also includes a synthetic mRNA leader, or more precisely a DNA region corresponding to the leader. Also included may be other transcriptional or translational control elements necessary or desirable to achieve or optimize expression, as discussed further below.

Accordingly, the expression system which is used to produce the desired gene product whose expression is enhanced can be any system from which a gene can be expressed, i.e. any system for the expression of a gene, more precisely for the expression of a recombinant gene. The expression system may be an in vivo or in vitro system and may for example be a vector, e.g. a plasmid (including e.g. phagemids or cosmids) or an artificial chromosome or a viral vector, or a construct (e.g. expression cassette) for insertion into a vector. The vector may be autonomously replicating or for chromosomal integration (e.g. a transposon-based vector or with sites for specific or homologous recombination for integration into the chromosome of the host cell into which the vector is introduced). The expression system according to the invention accordingly comprises a promoter, preferably a strong promoter, a region corresponding to a synthetic mRNA leader as defined herein and a gene which encodes the desired gene product or an insertion site for said gene.

A vector may be introduced into a host cell, and the host cell may be grown or cultured to allow said gene to be expressed, e.g. under conditions which allow the gene to be expressed. Such expression methods are well known in the art and widely described in the literature. The host cell may be any convenient or desired host cell, and may be prokaryotic or eukaryotic. Thus, all types of prokaryotic cells are included, most notably bacteria, and eukaryotic cells may include yeast or mammalian cells. Prokaryotic expression systems are however preferred and particularly bacterial expression systems. Accordingly the desired gene is preferably expressed in a bacterial host cell.

The desired gene product may be a heterologous gene product. In other words, a heterologous gene is expressed. The gene/gene product may be heterologous to the host cell used for expression. It may also be heterologous to the promoter and/or mRNA leader element(s) used, i.e. to the expression system. Thus, the desired gene need not be used with its native promoter or mRNA leader. Indeed, it is usual to design an expression system with a promoter which is not native to the gene it is desired to express, i.e. containing a particular promoter for expression and in general the promoter will not be native to the gene it is desired to express. In recombinant expression, a gene may be expressed with its native mRNA leader, although more usually an expression vector is designed to include a sequence encoding a leader for expression of the gene. According to the present invention, the synthetic mRNA leader, more particularly the mRNA leader elements, e.g. transcription- and/or translation-stimulating elements, need not be derived from the native leader of the desired gene, although this is encompassed herein, i.e. the unmodified mRNA leader may be the native leader of the desired gene and one or both mRNA leader elements may be modified leaders derived or adapted from leader of the desired gene. Thus, a synthetic mRNA leader comprising elements derived from any mRNA leader may be used, or put more particularly, a DNA region corresponding to such modified mRNA leader elements may be used. Thus, the elements in the region corresponding to the synthetic mRNA leader may be from, or may be derived from, any gene or any gene system (e.g. operon etc). The mRNA leader elements, e.g. transcription- and/or translation-stimulating elements, may be, or may be derived or adapted from, the leader which is native to the gene to be expressed, or it may be heterologous to the gene. It may, for example be, or may not be derived from, the unmodified mRNA leader (more precisely the unmodified mRNA leader-corresponding sequence) which occurs naturally with the promoter which is used for expression, i.e. which is native to the promoter. It may alternatively be non-native (heterologous) to both the promoter and the gene. Accordingly, the promoter and mRNA element(s) of the synthetic mRNA leader may be derived or adapted from those found naturally with the desired gene. Alternatively viewed, one or more of the promoter, region corresponding to the mRNA leader element(s) and gene may not occur naturally together. In some embodiments, for example, the one or more leader elements of the synthetic mRNA leader may be derived from a mRNA leader which occurs naturally together with the promoter, but not with the desired gene, i.e. the gene is heterologous, or alternatively, the one or both leader elements of the synthetic mRNA leader are derived from the mRNA "native" to the gene, but not the promoter.

In the methods of identifying the transcription- or translation-stimulating mRNA leaders (e.g. leader sequences or elements) the test mRNA leader may be produced by modifying a mRNA leader (e.g. introducing one or more mutations into a sequence corresponding to an unmodified mRNA leader, such as a native leader or a mutant leader which is already modified over its native form) or by generating an artificial sequence capable of functioning as a mRNA leader, e.g. by generating a random sequence as defined above.

A preferred mRNA leader element for use according to the present invention is or is based on that associated with the Pm promoter. In other words, the mRNA leader elements, e.g. transcription- and/or translation-stimulating elements, of the synthetic mRNA leader or identified by the methods described herein may be based on or derived or adapted from the mRNA leader associated with the Pm promoter. Thus, the "Pm" leader is preferred to be used as the leader to be mutated according to the present invention and as used herein the term "Pm mRNA leader" includes not only the native Pm mRNA leader as it occurs in nature, but also derivatives or variants thereof, e.g. Pm mRNA leader sequences which have been modified over the native "original" sequence. The original Pm mRNA leader is described in Inouye et al. (Gene, 29, 323-330, 1984). Pm mRNA leader derivatives or modified Pm mRNA leader sequences are described in Winther-Larsen et al. (Metabolic Engineering, 2, 92-103, 2000) and WO2008/015447, which are incorporated herein by reference.

Other representative mRNA leaders include the lac leader or derivatives thereof. The leaders from the promoters PT7ϕ10 and Ptrc and derivatives thereof can also be used. However, as mentioned above, in some embodiments, the mRNA leader elements may be derived or adapted from the native mRNA leader of the desired gene.

An expression system may contain any further elements necessary or desirable for expression, e.g. enhancer sequences. Regulatory features may also be present, e.g. start or stop codons, transcriptional initiators or terminators, ribosomal binding sites etc.

Further, selectable markers are also useful to include in the expression systems or vectors to facilitate the selection of transformants. A wide range of selectable markers are known in the art and are described in the literature. For example, antibiotic resistance markers can be used or the TOL plasmid Xyl E structural gene can be used. This encodes the product C230 which may readily be detected qualitatively or assayed. Spraying a plate of bacterial colonies with catechol rapidly distinguishes C230+ colonies since they turn yellow due to the accumulation of 2-hydroxy muconic semialdehyde, enabling transformants/transconjugants etc rapidly to be identified by the presence of xylE in the vectors.

As mentioned previously, in some embodiments the expression system may also comprise a reporter gene or tag, e.g. which may be translationally coupled to the gene of interest. Representative reporter genes include any antibiotic resistance gene e.g. bla, or any gene encoding a detectable product, e.g. mCherry, or an enzyme which catalyses a detectable reaction e.g. luc.

Translational coupling may be achieved using the phenomenon of translational reinitiation (Adkin and Van Duin, 1990, J. Mol. Biol., 213, 811-818; André et al., 2000, Febs Letters, 468, 73-78).

The expression system may conveniently be in the form of a vector, as mentioned above. As noted above, a range of vectors are possible and any convenient or desired vector may be used, e.g. a plasmid vector or a viral vector. A vast range of vectors and expression systems are known in the art and described in the literature and any of these may be used or modified for use according to the present invention. In a representative embodiment, vectors may be used which are based on the broad-host-range RK2 replicon, into which an appropriate strong promoter may be introduced. For example WO 98/08958 describes RK2-based plasmid vectors into which the Pm/xylS promoter system from a TOL plasmid has been introduced. Such vectors represent preferred vectors which may be used according to the present invention. Alternatively, any vector containing the Pm promoter may be used, whether in plasmid or any other form, e.g. a vector for chromosomal integration, for example a transposon-based vector. As noted above, the mRNA leader elements of the synthetic mRNA leader may be derived from the leader of the Pm promoter and accordingly, in one representative embodiment, the Pm promoter is used with a synthetic mRNA leader comprising one or more elements derived from the Pm mRNA leader.

Other vectors or expression systems which may be used include those based on or including the following promoters: Ptac, PtrcT7 RNA polymerase promoter ($P_7\phi10$), $\lambda P_L$ and $P_{BAD}$. The vectors may, as noted above, be in autonomously replicating form, typically plasmids, or may be designed for chromosomal integration. This may depend on the host organism used, for example in the case of host cells of *Bacillus* sp. chromosomal integration systems are used industrially, but are less widely used in other prokaryotes. Generally speaking for chromosomal integration, transposon delivery vectors for suicide vectors may be used to achieve homologous recombination. In bacteria, plasmids are generally most widely used for protein production.

As noted above, any prokaryotic or eukaryotic cell may be used for expression, but preferably, a prokaryotic cell. This includes both Gram negative and Gram positive bacteria. Suitable bacteria include *Escherichia* sp., *Salmonella, Klebsiella, Proteus, Yersinia, Azotobacter* sp., *Pseudomonas* sp., *Xanthomonas* sp., *Agrobacterium* sp., *Alcaligenes* sp., *Bordatella* sp., *Haemophilus influenzae, Methylophilus methylotrophus, Rhizobium* sp., *Thiobacillus* sp. and *Clavibacter* sp. In a particularly preferred embodiment, expression of the desired gene product occurs in *E. coli* or *Pseudomonas* sp., e.g. *Pseudomonas putida*. Eukaryotic host cells may include yeast cells or mammalian cell lines.

The desired gene product may be encoded by any desired or cloned gene, including partial gene sequences, or any nucleotide sequence encoding a desired expression product, including fusion protein products. Hence the term "gene" refers to any nucleotide sequence which it is desired to express.

The gene product may be any protein it is desired to produce. The term "protein" is used broadly herein to include any protein, polypeptide or peptide sequence. This may for example be a commercially or industrially important protein. Desired gene products may thus include therapeutically active proteins, enzymes or any protein having a useful activity, e.g. structural or binding proteins. Representative proteins may thus include enzymes involved in biosynthetic pathways or which make or are involved in the production of any useful product. Since the present invention is concerned with improving the production of commercially or industrially useful proteins, reporter genes or reporter gene products are not generally included as desired genes or desired gene products. However, as noted above, in some embodiments a reporter gene may be replaced by a desired gene, particularly when the expression product of the desired gene is readily and conveniently detectable, such that a classic reporter gene is not required.

As used herein, the term "mRNA leader" or mRNA leader sequence is equivalent to the term "5' untranslated region" or "UTR" and refers to the transcribed mRNA sequence between the transcription start site and translation start site in mRNA. The mRNA leader sequence hence is the transcribed sequence which begins at position +1 which relates to the transcription start site and continues until the translation start site. The region corresponding to the mRNA leader (sequence) occurs at the DNA level rather than the RNA level and may therefore also be viewed as the DNA (e.g. DNA sequence or region) which encodes the leader. The region corresponding to the mRNA leader may thus also be seen as the DNA which is the complement of the mRNA leader or which templates its synthesis. This is also known as the initial transcribed sequence (ITS) at the DNA level. Mutation of a region encoding a mRNA leader sequence can alter the transcription start site by two to three base pairs—in such a situation, +1 will relate to the 'new' transcription start site and hence the synthetic mRNA leader sequence in this case will again be defined as the sequence between +1 which relates to the transcription start site and the translation start site in mRNA.

The initial transcribed sequence (ITS) occurs at the DNA level as noted above and corresponds to or encodes the transcribed mRNA leader sequence. Hence, reference herein to introducing one or more mutations into a mRNA leader, refers to the mutation of the corresponding DNA sequence, i.e. the ITS sequence. Mutation of this region produces corresponding mutations in the mRNA leader sequence which is the transcribed ITS.

A mRNA leader sequence or element or its corresponding ITS can typically be from 10 to 40 nucleotides long, although it may be longer (e.g. up to 50, 60, 70, 80 or 100 or more nucleotides). For example, the mRNA leader or ITS may be 30 nucleotides long, or 25, 26, 27, 28 or 29 nucleotides long, but this may, of course, depend on the gene or promoter from which the mRNA leader is obtained or derived. As described above, any region encoding an mRNA leader sequence can be used in combination with any gene to be expressed and any appropriate promoter. However, in some embodiments, when the mRNA leader elements, e.g. transcription- and/or translation-stimulating elements, are mutated mRNA leaders, e.g. the mRNA leader that is mutated to generate one or both of said elements is native to either the promoter or the desired gene. As noted above a Pm mRNA leader sequence is preferred.

As used herein, the term "a strong promoter" refers to any strong promoter, which allows the gene under its control to be expressed at a high level. The strong promoter may be naturally occurring, or it may be a modified promoter or synthetic, e.g. a derivative of a naturally occurring promoter. It may thus be native or non-native. The term "strong promoter" is a well-known term in the art and strong promoters are widely described in the literature. Hence, such a promoter can produce large amounts of transcript and final protein product from the gene of interest. For example, strong promoters can express proteins at a level of at least 1% of the total cellular protein. Preferably, a strong promoter can express proteins at a level of 2, 5, 10, 15, 20, 25, 30, 35, 40, 45 or 50% of the total cellular protein. In the context of a secreted or exported protein (e.g. an extracellular protein or one supplied with a secretory sequence) levels of 1% or more, or more particularly of 2% or more, of total cellular protein may be viewed as high, and accordingly indicative of a strong promoter. For an intracellular protein, levels of 5% or 7% or more, more particularly 10% or more, may be viewed as indicative of a strong promoter. This may depend upon the expression system, host cell and conditions used etc. Accordingly, a promoter may be a strong promoter if it achieves the above expression levels at the selected conditions in the context of a particular host cell and expression system, i.e. it may be a strong promoter for the particular method and reagents used. Examples of strong promoters are well known in the art and any such promoters can be used in the expression system from which gene expression is enhanced. Such promoters for example include Pm promoter, Ptac, PtrcT7 RNA polymerase promoter ($P_7\phi10$), $\lambda P_L$ and $P_{BAD}$ or a derivative of any aforesaid promoter. Weak promoters are not included within the definition of strong promoters for the present invention and hence promoters such as $P_{CON}$ (Dobrynin et al., Nucleic acid Res. Symp. Ser., 7, 365-376, 1980) are excluded.

The promoter sequence can be found upstream of the transcription start site and is generally viewed as covering positions for example from −60 to −1, although this may vary. The promoter sequence hence does not include any of the transcribed sequence or the sequence at the DNA level which will be transcribed. The promoter sequence does not therefore cover any of the sequence downstream of and including +1.

The present invention is particularly useful in providing a means for improving protein production processes, particularly commercial or industrial protein production processes. Thus, the present invention can be used to improve, or bring up to a satisfactory or commercially-acceptable level, expression processes which are operating (i.e. expressing the protein) at a level which is not high enough for industrial purposes. However, as noted above, the invention may also be used to improve further processes or expression systems which are already working efficiently, e.g. where the levels of protein produced are acceptable at an industrial or commercial level.

Accordingly, alternatively viewed, the invention provides a method of enhancing expression of a desired gene product in a recombinant gene expression system, wherein said gene product is produced by expression of a gene and the expression of said gene is enhanced from an already efficient expression system, said method comprising expressing said gene using a synthetic mRNA leader as defined herein.

Furthermore, the invention provides a method of enhancing expression of a desired gene product in a recombinant gene expression system, wherein said gene product is produced by expression of a gene and the expression of said gene is enhanced from an already efficient expression system, said method comprising a method of optimizing a synthetic mRNA leader for the expression of a desired gene product according to the method described above and expressing said gene using said optimized synthetic mRNA leader.

The mRNA leader elements, e.g. transcription- and/or translation-stimulating elements, for use in the synthetic mRNA leader of the invention may be obtained by introducing one or more mutations into the DNA region corresponding to the mRNA leader. The mRNA leader elements, e.g. transcription- and/or translation-stimulating elements, that are capable of enhancing the transcription and/or translation of a heterologous gene can be identified using the methods described above.

In such alternatively viewed embodiments, an already efficient gene expression system may be seen as one which can express proteins at a level of at least 1% of the total cellular protein. Preferably, an already efficient expression system can express proteins at a level of 2, 5, 10, 15, 20, 25, 30, 35, 40, 45 or 50% of the total cellular protein. More particularly, for an exported or secreted protein the level may be 1% or more particularly 2% or more of total cellular protein and for an intracellular protein it may be 5% or more, or more particularly 7 or 10% or more. The considerations in relation to conditions and systems used, as mentioned above in the context of strong promoters, apply here also.

In embodiments in which the mRNA leader elements, e.g. transcription- and/or translation-stimulating elements, are mutated mRNA leaders, mutations can be made to the region which corresponds to the mRNA leader (i.e. to the ITS) at any one or more positions from the transcription start site to the translation start site. A mutation can consist of an addition or deletion or substitution of any one or more nucleotides in the ITS which results in the addition or deletion or substitution of any one or more nucleotides in the mRNA leader. Addition or deletion mutations may involve the addition or deletion of one or more base pairs. Hence, 1, 2, 3, 4, 5, 6, 7, 8, 9 or 10 or more bases can be inserted or deleted. In a particularly preferred embodiment, however, a mutation may be a substitution, which can occur at any position and may involve repetition (e.g. duplication) or inversion of fragments or segments of sequence. Hence, any of A, T(U), C or G can be substituted with a different base selected from A, T(U), C or G.

One or more mutations may be introduced to the ITS or mRNA leader. The one or mutations may be a combination of substitution, addition and/or deletion mutations or a number e.g. 2 or more additions or substitutions or deletions. Hence, a leader or ITS can contain for example both substitution and deletion mutations. Further, a leader or ITS may contain more than one substitution mutation at different positions in the leader. The length of the leader may also be increased, for example by introducing insertions or adding bases to one or both ends of the encoding sequence.

The number of mutations made is preferably in the range of 1 to 10, e.g. 2, 3, 4, 5, 6, 7, 8 or 9. For example, a mRNA leader or ITS may comprise 1, 2, 3, 4, 5, 6, 7, 8, 9 or 10 substitution mutations, or may comprise 1 substitution mutation and 1 or more (e.g. 2 or 3) deletion mutations. Alternatively, substitution and/or deletion mutations may be coupled with mutations which extend the length of the leader.

The one or more mutations can be introduced into the ITS from position +1 i.e. the transcription start site or further downstream of this position. In a preferred embodiment, particularly for leaders used to produce transcription-stimulating elements, mutations are not present at the transcription start site or near to it, for example not within positions +1 to +7. Hence, mutation(s) may be present at position +8 or downstream therefrom, for example from +8 to +40, more particularly at any one or more of positions +8, +9, +10, +11, +12, +13, +14, +15, +16, +17, +18, +19, +20, +21, +22, +23, +24, +25, +26, +27, +28, +29, +30, +31, +32, +33, +34, +35, +36, +37, +38 and/or +39. In the case of a longer or extended leader, mutations may be introduced at downstream positions up to the length of the leader, i.e. at any one of positions +8 up to the translational start site (from +8 to the end of the ITS). As previously described, any mutation, i.e. an addition, deletion or substitution can be made at any of these positions. Mutations can be introduced further downstream than position +20. For example at any one or more of residues +21, +22, +23, +24, +25, +26, +27, +28, +29 or +30 or further downstream, in the case of a longer leader. Thus, mutations can be introduced up to the translational start site at the end of the ITS.

Any such mutations may be generated by any method known in the art. For example, mutations may be made by mutagenesis which may be site directed or random. Random mutagenesis may be induced by chemically crosslinking agents or by radiation, for example exposure to UV light or may involve chemical modification of the nucleotides encoding or constituting the mRNA leader. Preferably mutations are introduced to the ITS sequence which corresponds to the mRNA leader at the DNA level. Further, the ITS can be mutated by using a 'doped' nucleotide mixture during its synthesis which corresponds to the mRNA leader, where at each step in polymerisation, the relevant wild type nucleotide is contaminated with the three other bases. This method enables the mutation frequency to be set at any particular level.

In a particularly preferred embodiment, the mutations introduced into the ITS or mRNA leader are non-predetermined mutations, or random mutations. Hence, the particular mutations which are introduced are not designed or specified before mutagenesis occurs. Thus, the mutations which occur are not predicted or determined. Any random mutagenesis method known in the art can be applied to produce the non-predetermined mutations e.g. radiation or using a 'doped' nucleotide mixture during mRNA leader synthesis as already described above. The introduction of non-predetermined mutations preferably refers to the initial screening stage of identifying mutations which enhance transcription and/or translation. Hence random mutagenesis is preferably used when producing test sequences, e.g. in methods of identifying transcription- and/or translation-stimulating elements for use in the synthetic mRNA leader of the invention. However, once such a mutation has been identified then it can be introduced into a mRNA leader sequence to produce a transcription- and/or translation-stimulating element by any mutagenesis method to provide the present invention. Therefore, in this way, a mutated mRNA leader can be selected as a transcription- and/or translation-stimulating element for use in the synthetic mRNA leader, which may be particularly suited to enhancing expression of a particular gene, e.g. in a preferred gene and promoter combination. However, mutated mRNA leaders which are found to enhance transcription and/or translation with one gene and/or promoter can also be used to enhance transcription and/or translation from a different gene and/or promoter. In other words, once a transcription- and/or translation-stimulating element has been identified it may be used with any other transcription- and/or translation-stimulating element for any gene, although it may be preferred to identity particular mutants for particular genes.

Further, in a preferred embodiment, the mutations introduced to the leader, particularly for leaders used to produce translation-stimulating elements, are not made to the Shine-Dalgarno sequence and/or do not establish or eliminate putative secondary structures. In some embodiments, particularly for leaders used to produce transcription-stimulating elements, the mutations do not include the insertion or creation of functional AU-rich sites, e.g. ribosomal protein binding sites (e.g. S1 binding sites), enhancer elements or U-rich sequences. In other embodiments, particularly for leaders used to produce translation-stimulating elements, the mutations may include the insertion or creation of functional AU-rich sites, e.g. ribosomal protein binding sites (e.g. S1 binding sites), enhancer elements or U-rich sequences. For example the insertion or creation of AU-rich tracts may or may not be included, e.g. AAGGAGGUGA (SEQ ID NO: 56), AAGGAGGU or AAGGAG.

The Shine-Dalgarno (SD) sequence is a short stretch of nucleotides located just upstream from most natural initiation codons with which the 3' end of 16S rRNA interacts. Usually, the Shine-Dalgarno sequence comprises GGAG nucleotides or a similar sequence, e.g. AGGA. Excluded mutations to this sequence, particularly for leaders used to produce translation-stimulating elements, can hence consist of substitutions to the sequence and extending or reducing the length of the SD sequence.

Further, in a preferred embodiment, the mutations made to the leader exclude the substitution of the entire leader sequence with a different leader sequence. Hence, in certain embodiments where the transcription- and/or translation-stimulating elements are mutant leader sequences, at least 50%, 60%, 70%, 80%, 90%, 95%, 96%, 97%, 98% or 99% of the sequence of the wild-type mRNA leader is retained compared to the mutated sequence (note that the "wild-type" leader is the "unmutated" leader and hence need not be a naturally occurring leader—it may include other modifications or may be a synthetic or artificial leader).

Alternatively viewed, where the mRNA leader elements, e.g. transcription- and/or translation-stimulating elements, are mutant leader sequences, each mutated leader sequence has at least 50%, 60%, 70%, 80%, 90%, 95%, 96%, 97%, 98% or 99% identity to the wild-type mRNA leader sequence from which it is derived. Identity may be determined using the BestFit program of the Genetics Computer Group (GCG) Version 10 Software package from the University of Wisconsin. The program uses the local homology algorithm of Smith and Waterman with the default values. Gap creation penalty=8, Gap extension penalty=2, Average match=2.912, Average mismatch=2.003.

In another preferred embodiment, the one or more mutations which are introduced to the mRNA leader do not alter its secondary structure, e.g. do not alter or change or create or eliminate hair pin loop or other secondary structures.

Hence in a most preferred embodiment where the transcription- and/or translation-stimulating elements are mutant leader sequences, one or more non-predetermined substitution mutations are introduced to the mRNA leader sequence but not to the Shine-Dalgarno sequence.

Although the mRNA leader elements, e.g. transcription- and/or translation-stimulating elements, may be derived from any mRNA leader, i.e. any mRNA leader can be mutated in the present invention; in a preferred embodiment the invention uses the mRNA leader sequence which occurs naturally with the Pm promoter (a "Pm mRNA leader") which includes derivatives of the native sequence. Hence, in one embodiment according to the present invention, one or more mutations may be made to the sequence aactagtacaataataatggagtcatgaacatatg (SEQ ID NO: 1) which is the DNA sequence (or ITS) corresponding to a Pm leader. A representative transcription-stimulating element, which is a mutant Pm mRNA leader, may have a sequence selected from SEQ ID NOs: 18-23, preferably selected from any one of SEQ ID NOs: 21-23 as shown in Table 1. A representative translation-stimulating element, which is a mutant Pm mRNA leader, may have a sequence selected from SEQ ID NOs. 25-46, preferably selected from any one of SEQ ID NOs: 32, 41, 42 and 45 as shown in Table 1. Thus, a synthetic mRNA leader of the invention may comprise a transcription-stimulating element selected from SEQ ID NOs. 21-23 and/or a translation-stimulating element selected from SEQ ID NOs: 32, 41, 42 and 45. A particularly preferred synthetic mRNA leader may comprise a transcription-stimulating element comprising SEQ ID NO: 21 and a translation-stimulating element comprising SEQ ID NO: 42. However, it will be understood that these mutants were identified by screening using particular genes. As explained above, the effects of the mutations may in some cases and/or to some degree be gene-specific or gene-dependent. Accordingly, whilst it may be the case that some mutants may be useful with different genes, particular mutants are not generally regarded to be of universal application, and generally mutants will be selected for particular genes.

Thus, the present invention therefore encompasses a synthetic mRNA leader sequence as defined above. Also included is the DNA sequence (ITS) corresponding to the said synthetic mRNA leader.

The Pm mRNA leaders can be mutated at any one of positions +1 to +35 and as described previously such mutations can be selected from any one or more of a substitution mutation, a deletion mutation and an addition mutation. Preferably, positions +4 and +7 are not mutated.

Mutations are hence preferably found within the range of position +2 to position +27, more preferably within the range from position +2 to +18, for example mutations maybe found at one or more of +2, +3, +5, +6, +8, +9, +10, +11, +12, +13, +14, +15, +16 and +17.

Vectors comprising the synthetic mRNA leader or ITS sequences of the invention and cells and libraries comprising such vectors or the synthetic mRNA leader sequences are also encompassed.

The synthetic mRNA leader, or more particularly the ITS, can be used to enhance expression of any gene product. However, in a preferred embodiment, the ITS can be mutated and specific mutants tailored for the enhanced expression of a particular gene may be selected. Hence, such mutants may be identified by using them in an expression system with the desired gene and the mutants giving the highest levels of enhanced expression may be selected. Such mutant ITS sequences may be selected and sequenced. These sequences, although specifically selected for enhanced expression of one gene can however still be used for the enhanced expression of other genes.

A further aspect of the present invention includes a method of obtaining a synthetic mRNA leader mutant capable of enhancing the expression of a desired gene, said method comprising:

(a) introducing one or more mutations into the DNA corresponding to a synthetic mRNA leader of the invention;

(b) selecting a synthetic mRNA leader mutant from (a) which enhances expression of the said desired gene.

More particularly, this aspect of the invention provides a method of obtaining a synthetic mRNA leader mutant capable of enhancing the expression of a desired gene, said method comprising:

(a) introducing one or more mutations into the DNA corresponding to a synthetic mRNA leader of the invention;

(b) expressing said desired gene using said synthetic mRNA leader mutant in a host cell; and (c) selecting an synthetic mRNA leader mutant which enhances expression of said desired gene.

Preferably the gene is desired to be expressed using a strong promoter or in an already efficient expression system and/or is a heterologous gene.

The step of introducing the mutations can be seen to generate a library of synthetic mRNA leader mutants (more precisely ITS mutants or mutants of the region corresponding to the leader). This library may then be screened to select a mutant which enhances expression of a desired gene.

The library may contain two or more mutants, preferably 3, 4, 5, 6, 8, 10, 12, 15, 18, 20, 22, 25, 30, 40, 50, 100, 200, 500, 1000, 5000, 10000, 50000, 100000, 200000, 500000 or more mutants.

The method of this aspect of the invention may thus be seen as a method for screening or identifying or selecting synthetic mRNA leader mutants.

The one or more mutations can be introduced into the ITS by any method already described above, although in a most preferred embodiment, one or more mutations are introduced by using a "doped" nucleotide mixture at each step in the polymerisation of the synthesis of one strand of a synthetic oligonucleotide covering the synthetic mRNA leader.

As described above, the methods of screening can be used to select a mutant ITS which is tailored or selected for particularly high enhanced expression for a particular gene, although such mutants can in any case then be used to enhance expression of other gene products.

The selection of a synthetic mRNA leader or ITS mutant which can enhance expression of the desired gene product by enhancing transcription and/or translation may be carried out using methods well known in the art. For example, the activity of the gene product can be measured, e.g. by ELISA or a similar assay, and the activity obtained using the mutant synthetic mRNA leader can be compared to that obtained using the wild type leader. Hence, a comparison of the activity levels obtained when using both the original synthetic mRNA leader and the mutant synthetic mRNA leader sequences will identify those mutants which have enhanced protein activity and hence gene expression. Once such enhanced expression mutants have been identified transcriptional effects can be investigated, if desired, for example by determining transcript levels. Transcript levels may be measured or assessed as described above. Alternatively transcript levels may be directly assessed or determined to select the mutants. A mutant synthetic mRNA leader or ITS can be assessed for its ability to enhance gene expression by either investigating the levels of a reporter gene product which is produced (which can either be produced on its own, or as a fusion protein with the desired gene product, or more advantageously by translational coupling of reporter gene expression to the expression of the desired gene), or by directly investigating the levels of desired gene product produced.

Hence, in a preferred embodiment the selecting step may involve the assessment or determination of levels or the activity of a reporter gene. In a particularly preferred embodiment the reporter gene is an antibiotic resistance marker e.g. bla or encodes a detectable product, e.g. mCherry, or a product which results in the production of a detectable product e.g. luc or celB. Therefore, mutant synthetic mRNA leaders which can enhance expression can be screened for example by detecting colonies of cells transformed with the expression system comprising a promoter, mutant mRNA leader and reporter gene, which can grow on media containing high concentrations of penicillin (when the reporter gene is bla) or other antibiotic. For example, a penicillin concentration in the range 1-15 mg/ml, may be used to select high expressers but this can be reduced by using a construct designed in a particular way, for example, having a mutation in the Shine-Dalgarno sequence to reduce translation. This would provide a wider window for identification of transcriptional stimulation, because addition of more than 15 mg/ml penicillin is impractical. Alternatively, the amount of gene product obtained with the mutant mRNA leader can be measured using for example Western blotting and compared to that obtained when using the original synthetic mRNA leader. Those mutants having enhanced expression as defined herein are selected in accordance with the present invention. Such a method may not be practical for low frequency mutants.

In a further embodiment, the invention provides a method of obtaining a synthetic mRNA leader mutant which is capable of enhancing expression of a desired gene, said method comprising the steps of:
  a) introducing one or more mutations into the synthetic mRNA leader sequence of the invention;
  b) producing a library comprising the mutant synthetic mRNA leader sequences upstream of the gene of interest or of a reporter gene; and
  c) screening the library for synthetic mRNA leader mutants which enhance expression of said desired gene or reporter gene.

In this way, a library of mutated synthetic mRNA leader sequences can be screened, wherein clones expressing protein at the required levels can be selected using methods described above e.g. Western blotting, or by using a reporter gene e.g. bla. By using the desired gene of interest in the method of screening, mutant ITS sequences which are tailored or optimum or selected for enhanced expression of that gene can be selected. If a reporter gene alone is used in the method of screening, then mutated ITS sequences which may have general application may be selected.

However, since the effects of the mutants can be gene-dependent, it is preferred to select the mutants with reference to the desired gene. Since it would be laborious to design and construct separate expression systems for every desired gene, the inventors have devised a method for optimizing the synthetic mRNA leader of the invention for the expression of a desired gene product, as described above.

The method uses the Ribosome binding site (RBS) calculator described by Salis et al., 2009 (Nat Biotechnol 27: 946-950) and Borujeni et al., 2013 (Nucleic Acid Research, 41(4) pp. 2646-2659 and https://salis.psu.edu/software/) to determine the translational initiation rate (TIR) of the synthetic mRNA leader. Thus, the step of determining the TIR preferably is based on the sequence of the whole translation-stimulating element in combination with initial sequence of the desired heterologous gene, e.g. up to 50 nucleotides for each sequence. However, the translation-stimulating element may comprise more than 50 nucleotides. Accordingly, the input sequence used may be up to 50 nucleotides of the element from the 3' end, e.g. up to 35, 40, 45 or 50 nucleotides. The initial sequence of the desired heterologous gene may include up to the first 50 nucleotides of the desired gene from the 5' end, e.g. up to 35, 40, 45 or 50 nucleotides. However, a longer input sequence for the translation-stimulating element and/or the desired heterologous gene may be used in some embodiments, e.g. at least 50, 55, 60, 65, 70, 80, 90 or 100 nucleotides.

Applying the forward engineering function of the RBS calculator means that the sequence of the translation-stimulating element may be modified, i.e. by introducing one or more mutations as defined herein, to increase the TIR value or score, preferably to maximise the TIR value, for the desired gene, i.e. increase the value above the initial value calculated in the determining step.

Selecting a translation-stimulating element with a higher TIR value (i.e. an optimized translation-stimulating element) means selecting a sequence that is calculated to have a higher TIR value than the initial input sequence. In some embodiments, the method may include a step of synthesizing the selected sequence, e.g. synthesizing the sequence de novo or modifying the sequence of the initial element to generate the selected, optimized, sequence.

As discussed above, the spacer region of the synthetic mRNA leader of the invention may function to facilitate the modification of the leader. Accordingly, the optimized translation-stimulating element may be inserted into a nucleic acid molecule comprising a synthetic mRNA leader, e.g. to replace the translation-stimulating element, thereby generating an optimized synthetic mRNA leader. In some embodiments, the nucleic acid molecule comprising the synthetic mRNA leader also contains the desired heterologous gene (i.e. the nucleic acid molecule is an expression cassette or operon), wherein the optimized translation-stimulating element is inserted upstream of the desired heterologous gene and downstream of the transcription-stimulating element. In some embodiments, the optimized translation-stimulating element is inserted into a nucleic acid molecule to produce an optimized synthetic mRNA leader, e.g. the desired gene can be inserted into the nucleic acid molecule later or the optimized synthetic mRNA leader may be transferred into an operon containing the desired gene. Thus, the optimized translation-stimulating element is inserted downstream of the transcription-stimulating element.

In some embodiments, e.g. in methods for optimizing the synthetic mRNA leader for a desired gene, the desired (test) gene may be inserted into an expression vector downstream of a promoter and the synthetic mRNA leader (or the insertion site for the synthetic mRNA leader) and a reporter gene is inserted as a second gene in such a way that its translation is coupled to the translation of the upstream gene (the desired or test gene) through overlapping or closely positioned stop and start sites. Thus, the level of expression of the desired gene determines the level of expression of the reporter gene. Reporter gene expression is thus an indicator of the level of desired gene expression, and may be determined to determine desired gene expression. Convenient reporter genes to use are antibiotic resistance genes for example bla or the kanamycin resistance gene. Any desired gene may thus be inserted into such an operon, which may contain nucleotide sequence for selection, i.e. a potential transcription- and/or translation-stimulating element. A library of potential transcription- or translation-stimulating elements (e.g. mutant mRNA leaders) may be generated in such an operon, which may be inserted into a vector, e.g. a "screening vector". A screening vector for identifying a transcription- or translation-stimulating element preferably comprises a polycistronic operon as defined above.

Accordingly, in a preferred embodiment, an artificially constructed operon as defined herein can be used to screen mutant ITS/mRNA leader sequences (e.g. leader elements) in a library or otherwise. Such an operon may be contained in any convenient vector, for example in a plasmid. Such an operon typically incorporates the desired gene whose expression is to be enhanced and at least one reporter gene, conveniently an antibiotic resistance marker gene e.g. bla (which encodes beta-lactamase and confers resistance to penicillin as previously described). The desired gene is positioned upstream of a reporter gene. In some embodiments, the desired gene may be translationally coupled to a reporter gene. Whilst the transcription of the desired gene and reporter gene(s) is linked, the translation of the reporter gene (i.e. the reporter gene that is not translationally coupled to the desired gene) is independent of the desired gene. The vector further comprises the mutant mRNA leader element sequence and promoter upstream of the gene of interest. Hence, the desired gene product is produced together with, but independently from, a reporter gene and in such a way, the expression of the reporter gene can be used to measure the expression of the desired gene.

By determining the level of reporter gene expression, the level of desired gene expression may be determined.

Potential mRNA leader elements, e.g. transcription- or translation-stimulating elements such as mRNA leader mutants, which enhance expression of the desired gene may be determined by comparing the level of expression (i.e. reporter gene expression) with that obtained using the corresponding unmodified leader.

Thus to determine the level of expression, a said vector is introduced into a host cell, and said host cell is cultured or grown to allow said desired and reporter genes to be expressed (e.g. under conditions which allow said genes to be expressed).

The promoter is preferably a strong promoter.

The potential transcription- or translation-stimulating element library (e.g. mutant mRNA leader element library, i.e. test nucleotide sequence library) can be made in prokaryotic cells, preferably in E. coli. Other cell types can be used to create the library, examples of which have been described supra. Hence, libraries can be created using for example the expression systems already described or the artificially constructed operon. Such a library is plated onto agar plates, where the number of transformants may be about 100000 or more, e.g. 200000, 300000 or more. Clones containing the artificially constructed operon can be selected for by antibiotic resistance, e.g. by resistance to ampicillin, where such a resistance gene is also present in the operon or vector containing the operon. Appropriate selectable markers have been discussed supra. High expression mutants can be screened for by detecting enhanced expression of the reporter gene or the desired gene product and can be sequenced to identify the mutation(s) responsible for enhanced expression.

As noted above, the methods of the invention find particular utility in the commercial or industrial production of proteins. In a preferred aspect, therefore the methods of producing a protein or of enhancing expression of a protein relate to production-scale processes i.e. they are carried out on a production-scale or industrial scale, rather than a laboratory experiment. The processes may be preferred in a bio-reactor or fermentor, particularly a production-scale bio-reactor or fermentor.

The invention will now be described in more detail in the following non-limiting Example with reference to the following drawings:

FIG. 1 shows the structure of the synthetic polycistronic operons in plasmids pAO-Tr and pAO-Tn, which are used to identify transcription- and translation-stimulating elements. Both synthetic operons (A and B) are transcribed from the inducible Pm promoter (see arrow) and contain celB (encoding phosphoglucomutase) and bla (encoding β-lactamase). SD: Shine-Dalgarno sequence. t: transcriptional terminator. The unique PciI and NdeI restriction endonuclease sites were used for the insertion of the degenerated oligonucleotides. A vector containing operon A is designated pAO-Tr and a vector containing operon B is designated pAO-Tn. Pm 5'-UTR variants identified in pAO-Tr were called Tr-UTRs and variants identified in pAO-Tn were named Tn-UTRs.

Figure 2:
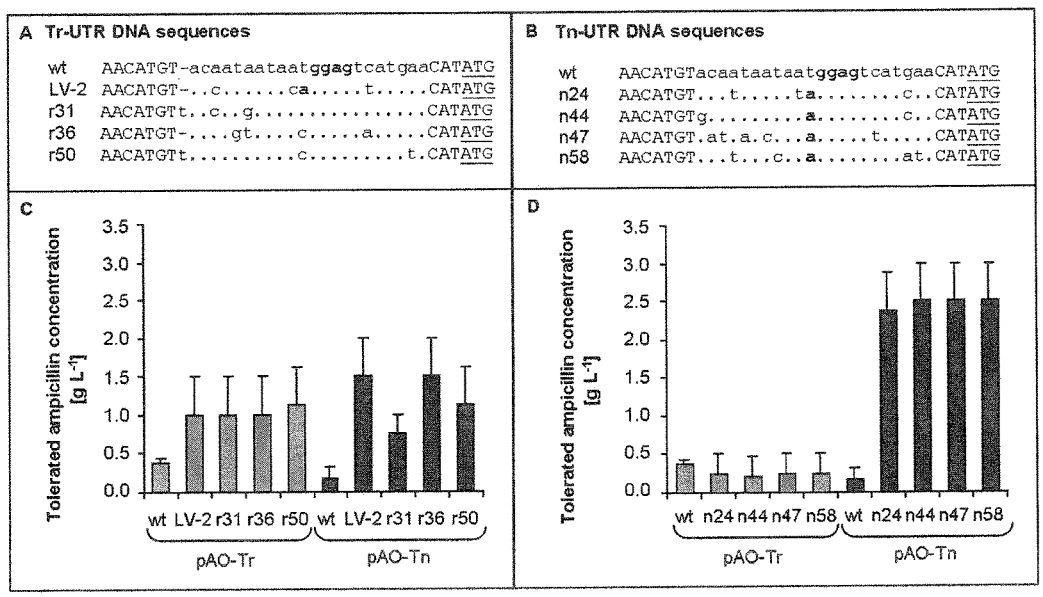

FIG. 2 shows 5'-UTR DNA variants identified by screening pAO-Tr- and pAO-Tn-based 5'-UTR libraries for high bla expression and positional effects of these variants on expression. r31 (SEQ ID NO: 21), r36 (SEQ ID NO: 22), r50 (SEQ ID NO: 23) are 5'-UTR variants that were identified from the Tr-UTR library (A) while n24 (SEQ ID NO: 32), n44 (SEQ ID NO: 41), n47 (SEQ ID NO: 42), n58 (SEQ ID NO: 45) are candidates from the Tn-UTR library (B). The wild-type (wt) UTR is set forth in SEQ ID NO: 1; LV-2 (SEQ ID NO: 18) is a control 5'-UTR variant that was previously shown to display transcription-stimulating abilities. Nucleotides that were not mutagenized are typed in capital letters. These include the PciI (ACATGT) and NdeI sites (CATATG). The putative SD sequence is highlighted in boldface. The ATG start codon (part of the NdeI site) is underlined. Synthetic oligonucleotides carrying different mutations were inserted into both pAO-Tr and pAO-Tn using PciI and NdeI (FIG. 1) and transferred to E. coli DH5a. The resulting strains harboring vectors with Tr-UTR DNA sequences (C) or Tn-UTR DNA sequences (D) were first grown in liquid medium overnight, then diluted 1:10.000, and finally transferred to agar media containing increasing ampicillin concentrations and 0.1 mM m-toluate. This low concentration was used initially to make sure resistance levels were in a range allowing us to distinguish moderate phenotypic differences among clones. Results are presented as averages of the highest ampicillin concentrations at which growth was observed. Error bars point to the next tested ampicillin concentration (at which no growth was observed).

Figure 3:
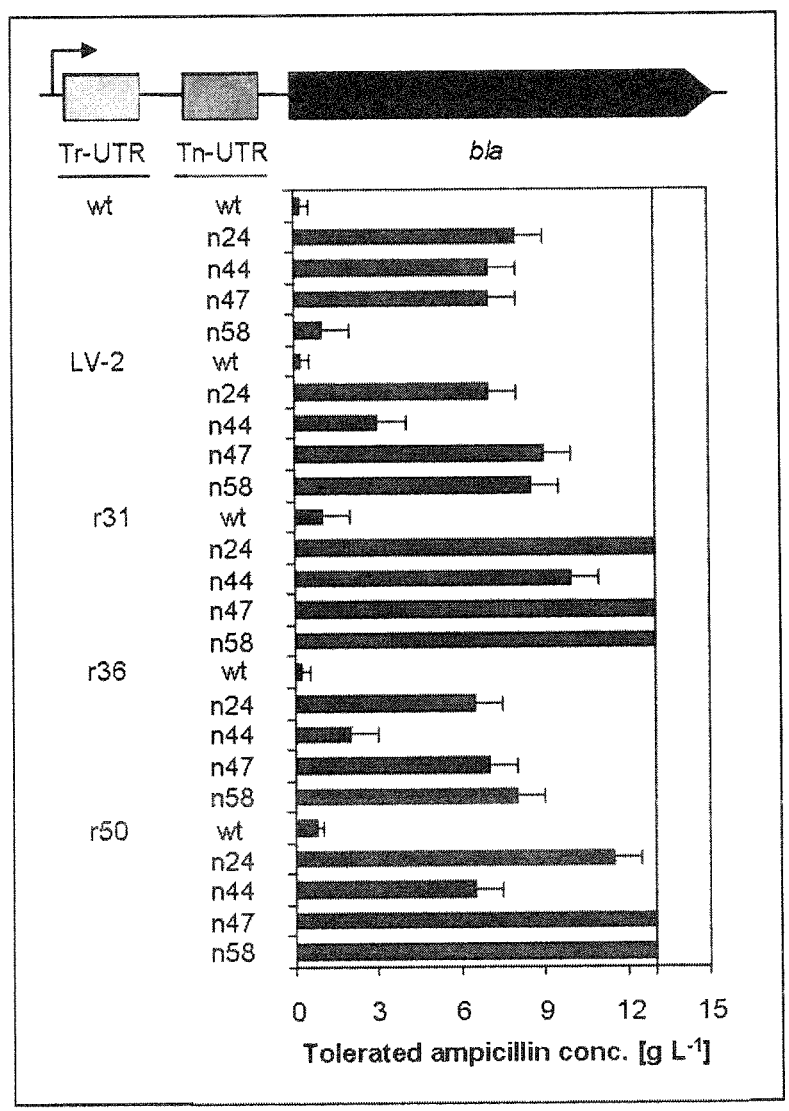

FIG. 3 shows analysis of how combinations of variant Tr- and Tn-UTR elements affect ampicillin host tolerance in the dualUTR context. Besides the wt-UTR four different Tr- and Tn-UTRs were selected and all 25 possible combinations were used in host ampicillin tolerance experiments, as described in the legend to FIG. 2, except that here 2 mM m-toluate was used. Thirteen g $L^{-1}$ was the highest concentration tested, as indicated by a vertical line. Error bars point to the next tested ampicillin concentration (at which no growth was observed). The UTR sequences referred to in FIG. 3 are defined in the legend for FIG. 2, above.

Figure 4:
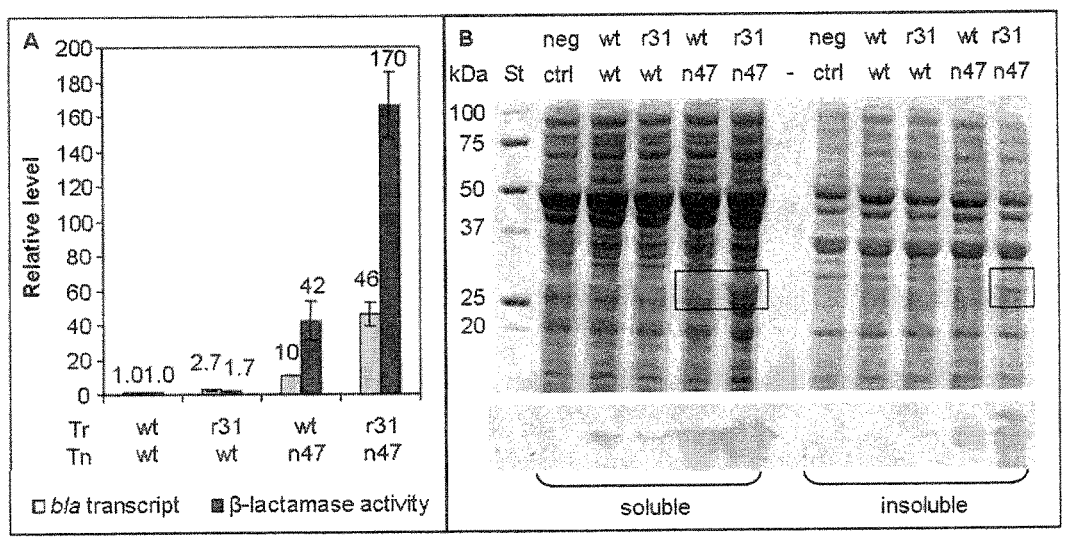

FIG. 4 shows β-lactamase production analysis in E. coli strains harbouring plasmids with r31Tn- and Trn47-dualUTR combinations. (A) Recombinant E. coli DH5a strains were grown in LB until $OD_{600}$~0.1 when expression was induced with 2 mM m-toluate. Five hours post induction samples were collected for transcript and β-lactamase activity. The value for the wtwt combination was arbitrarily set to 1.0. Average and standard deviation stem from three replicas. (B) Recombinant E. coli RV308 (ATCC31608) strains were cultivated in superbroth and induced with 2 mM m-toluate at $OD_{600}$=0.6-0.8 Protein gel of cell lysates that were separated into the soluble (supernatant) and insoluble (pellet) fraction. Results from one representative experiment are shown. Visible β-lactamase bands are highlighted with a box. β-lactamase activity was also determined and the data corresponded to the data generated in the E. coli DH5a strains (data not shown). St: Precision Plus Dual Color Protein standard (Bio-Rad); neg ctrl: plasmid-free E. coli RV308. The UTR sequences referred to in FIG. 4 are defined in the legend for FIG. 2, above.

Figure 5:
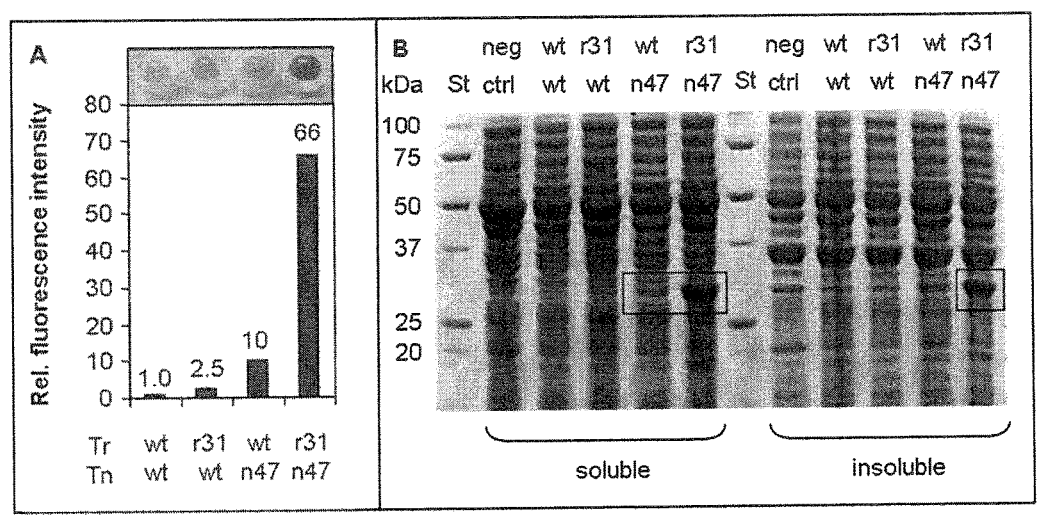

FIG. 5 shows mCherry production analysis in E. coli RV308 (ATCC31608) strains harbouring plasmids with r31Tn- and Trn47-dualUTR combinations. Results from one representative experiment are shown. (A) Fluorescence intensities were determined directly from the cultures, normalized against $OD_{600}$ followed by relating all values to the values obtained from strains harbouring vectors with the wtwt-dualUTR combination. The image at the top shows pellets from the four different cultures at the harvesting time point. (B) SDS-PAGE gel of E. coli RV308 strains producing mCherry. St: Precision Plus Dual Color Protein standard (Bio-Rad); neg ctrl: plasmid-free E. coli RV308. The UTR sequences referred to in FIG. 5 are defined in the legend for FIG. 2, above.

Figure 6:
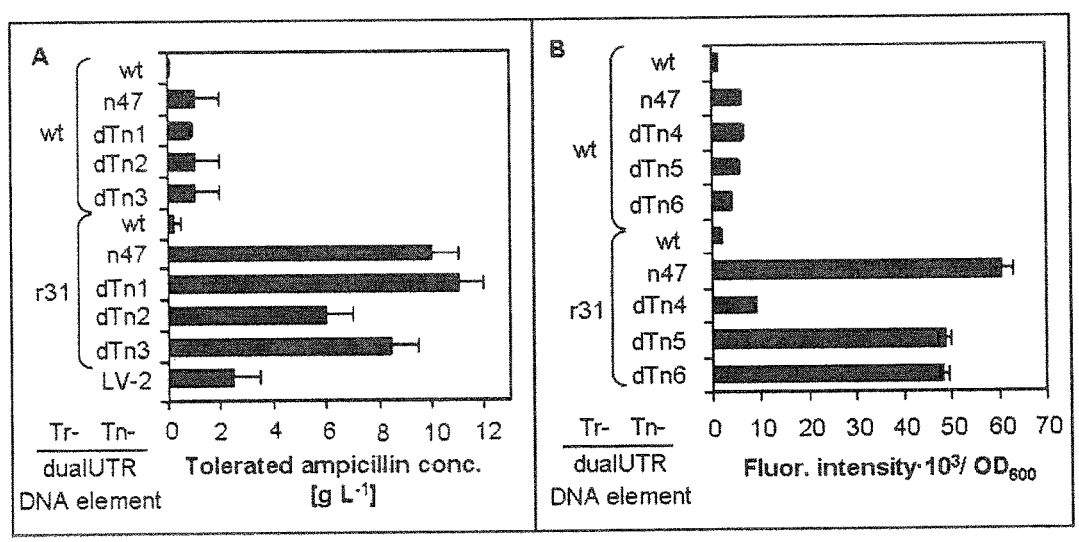

FIG. 6 shows a comparison of effects on expression of experimentally generated Tn-dualUTR DNA elements with those designed by the forward engineering function of the RBS calculator. Results were obtained after induction with 0.1 mM m-toluate. (A) Ampicillin tolerance analysis. Bars indicate the highest ampicillin concentrations at which growth was observed. Error bars point to the next tested ampicillin concentration (at which no growth was observed). A strain harbouring a construct in which the short LV-2 UTR DNA sequence was inserted upstream of the bla gene to relate the effects of the dualUTR sequences to those reported previously for LV-2 (Berg et al., (2011) J. Biotechnol. 158: 224-230). (B) Strains producing mCherry were grown in 96-well plates. At harvest, fluorescence intensities were normalized against $OD_{600}$ to calculate averages and standard deviations obtained from four parallel cultures. The sequences of the wt, r31 and LV-2 UTRs are defined in the legend for FIG. 2, above. The dTn1 UTR has the sequence set forth in SEQ ID NO: 50; the dTn2 UTR has the sequence set forth in SEQ ID NO: 51; the dTn3 UTR has the sequence set forth in SEQ ID NO: 52; the dTn4 UTR has the sequence set forth in SEQ ID NO: 53; the dTn5 UTR has the sequence set forth in SEQ ID NO: 54; the dTn6 UTR has the sequence set forth in SEQ ID NO: 55.

Figure 7:
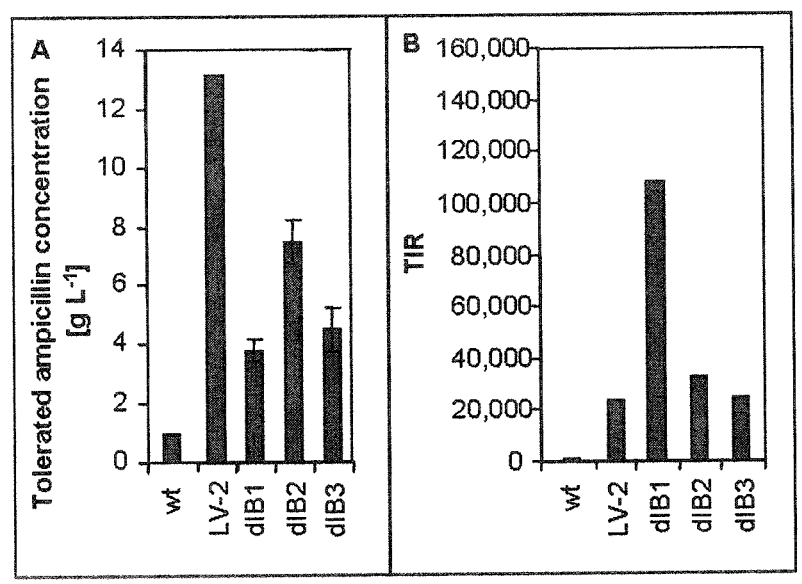

FIG. 7 shows the effect on β-lactamase production of short 5'-UTR DNA sequences predicted by the RBS calculator. (A) Relative change of ampicillin tolerance of strains expressing bla coupled to DNA regions corresponding to different 5'-UTRs (wild-type (SEQ ID NO: 1) set to 1). Results were obtained from replica plating using increasing ampicillin concentrations and inducing expression with 2 mM m-toluate. The 5'-UTR variants included the previously identified LV-2 variant (Berg et al., (2009) Microb. Biotechnol. 2: 379-389; SEQ ID NO: 18) and three designed 5'-UTR DNA sequences (dIB1 (SEQ ID NO: 47); dIB2 (SEQ ID NO: 48); and dIB3 (SEQ ID NO: 49)). 13 g was the highest ampicillin concentration used. (B) Analysis of the translation initiation rates (TIR) of different UTR-b/a sequences according to the RBS calculator.

Figure 8:
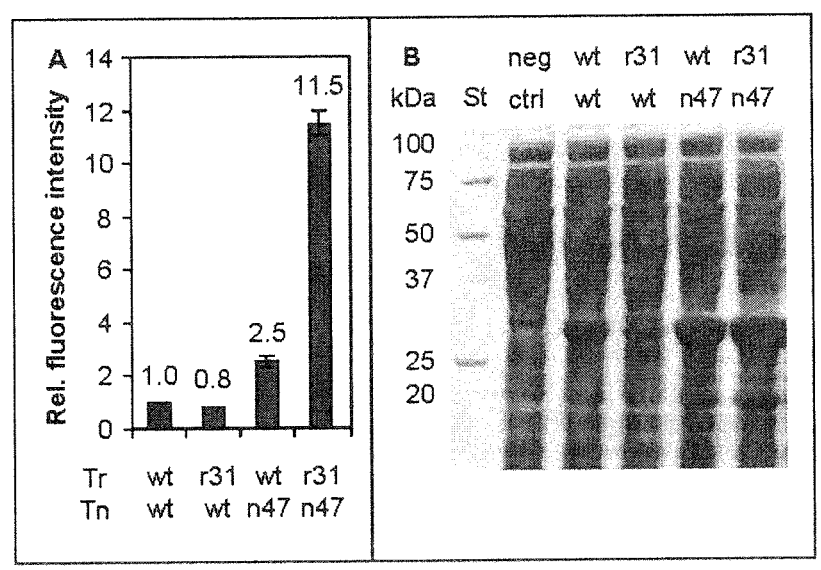

FIG. 8 shows the transfer of selected pDUTRc constructs to P. putida KT2440 and resulting effects on mCherry production. Constructs with combinations of dualUTR DNA elements wtwt, r31 wt, wtn47 and r31n47 were transferred to P. putida KT2440. Recombinant strains were grown in LB medium at 30° C. and mCherry production was induced with 1 mM m-toluate. (A) 4 hours post induction, fluorescence intensities of the different cultures were determined, normalized against $OD_{600}$ and related to the values from strains harbouring the wtwt-dualUTR combination. Data originate from two independent experiments. (B) SDS-PAGE of the soluble protein fraction. St: Precision Plus Dual Color Protein standard (Bio-Rad); neg ctrl: plasmid-free P. putida KT2440. The UTR sequences referred to in FIG. 8 are defined in the legend for FIG. 2, above.

EXAMPLES

Materials and Methods

Bacterial Strains and Growth Conditions

Recombinant E. coli DH5α (Bethesda Research Laboratories), E. coli RV308 (ATCC 31608) and P. putida KT2440 were cultivated in Lysogeny broth (LB) (10 g $L^{-1}$ tryptone, 5 g $L^{-1}$ yeast extract and 5 g $L^{-1}$ NaCl) or on LB agar (LB broth with 15 g $L^{-1}$ agar) supplemented with 0.05 g $L^{-1}$ kanamycin unless stated otherwise. Selection of E. coli DH5α transformants was performed at 37° C., while 30° C. was used for all growth experiments. Induction of the XylS/Pm system was accomplished by addition of varying m-toluate (3-methylbenzoate) concentrations.

DNA Manipulations

DNA fragments were extracted from agarose gels using the QIAquick® gel extraction kit and from liquids using the QIAquick® PCR purification kit (QIAGEN). Plasmid DNA was isolated using the Wizard® Plus SV Minipreps DNA purification kit (Promega) or the NucleoBond® Xtra Midi kit (Macherey-Nagel). Synthetic oligonucleotides were ordered from Sigma-Aldrich or Eurofins MWG Operon. Restriction cloning was performed according to recommendations from New England Biolabs. PCR reactions were carried out with the Expand High Fidelity PCR System (Roche Applied Science). E. coli strains were transformed using a modified RbCI protocol (Promega) and P. putida KT2440 was transformed with a electroporation protocol. Genetic constructs were confirmed by sequencing performed at Eurofins MWG Operon or GATC Biotech using primer 5'-AACGGCCTGCTCCATGACAA-3' (SEQ ID NO: 2) for pAO-Tr-, plB11-, pDUTR- and pDUTRc-based constructs and primers 5'-CTTTCACCA-GCGTTTCTGGGTG-3' (SEQ ID NO: 3) or 5'-CAAGGATCTTACCGCTGTTG-3' (SEQ ID NO: 4) for pAO-Tn-based constructs (see below).

Vector Constructions

All vectors are based on the mini-RK2 replicon (four-seven plasmid copies per chromosome), containing the xylS/Pm expression cassette, and kanamycin resistance gene.

(i) Construction of the pAO-Tr and pAO-Tn Screening Vectors

Two vectors containing synthetic bicistronic operons were designed to facilitate the identification of primarily transcription- or translation-stimulating mutations within Pm 5'-UTR DNA sequences.

pAO-Tr The bla gene was amplified from plasmid plB11 with the primers 5'-GCAGGCGGAATTCTAATGAGGT-CATGAACTTATGAGTATTCAACATT-3' (SEQ ID NO: 5) and 5'-CTAGAGGATCCCCGGGTACCTTTTCTACGG-3'

(SEQ ID NO: 6), introducing the restriction sites EcoRI and BamHI, and was cloned into the pIB22 plasmid as EcoRI-BamHI fragment downstream of the celB gene. pIB22 is a derivative of pLB11, where an EcoRI restriction site was introduced downstream of the celB gene. This resulted in plasmid pAO-Tr.

pAO-Tn The celB gene and the DNA sequence corresponding to its 5'-UTR were PCR amplified using primer pair 5'-ACCCCTTAGGCTTTATGCAACAgaaACAATA ATAATGGAGTCATGAACtTATG-3' (SEQ ID NO: 7) and 5'-CTTTCACCAGCGTTTCTGGGTG-3' (SEQ ID NO: 8) from the pAO-Tr plasmid. The resulting PCR product was digested with Bsu36I and EcoRI and re-introduced into pAO-Tr using the same restriction sites leading to pAO-Tn (−1). By this procedure, additional NdeI and PciI sites were removed (indicated by small letters). The bla gene was PCR amplified using primer pair 5'-cggaattCAACATGTA-CAATAATaatg-3' (SEQ ID NO: 9) and 5'-AGCTAGAG-GATCCCCGGGTA-3' (SEQ ID NO: 10) and the resulting PCR product was cloned as EcoRI-BamHI fragment into the pAO-Tn(−1) plasmid resulting in pAO-Tn.

(ii) Construction of Vectors to Characterize Different 5'-UTR Variants

Generally, 5'-UTR DNA sequences were integrated between the unique PciI and NdeI sites of plasmid pIB11 as annealed pairs of forward and reverse synthetic oligonucleotides.

pDUTR was generated based on pIB11 by replacing the Pm 5'-UTR DNA region with annealed oligonucleotides 5'-<u>CATGT</u>ACAATAATAATGGAGTCATGAACATATCTT-CAT GAG<u>CTC</u>CATTATTATTGTATATGTAC-AATAATAATGGAGTCATGAA<u>CA</u>-3' (SEQ ID NO: 11) and 5'-<u>TATG</u>TTCA-TGACTCCATTATTATTGTACATATACAATAATAATG GAGCTCATGAA GATATGTTCATGACTCCATTATTAT-TGTA-3' (SEQ ID NO: 12). Restriction sites PciI (partial), SacI and NdeI (partial) are underlined.

pDUTRc contains an *E. coli* codon-optimized version of the mCherry gene, which was PCR-amplified using primers 5'-GCTGCATATGGTTTCTAAAGGTGAAGAAG-3' (SEQ ID NO: 13) and 5'-GCTCGGATCCTTATCATTTATACA-GTTCGTCCATAC-3' (SEQ ID NO: 14) and digested with NdeI and BamHI to replace the bla gene in pDUTR.

pDUTR and pDUTRc Derivatives

Annealed synthetic oligonucleotides flanked by PciI and SacI (Tr-dualUTR DNA element) and SacI and NdeI (Tn-dualUTR DNA element) sticky ends, respectively, carrying mutations according to their Tr- and Tn-UTR counterparts were inserted into pDUTR or pDUTRc using the appropriate restriction enzymes. Combined, the UTR variants originating from the pDUTR and pDUTRc vector variants are called TrTn-dualUTRs in which 'Tr' and 'Tn' can be replaced with the name of a certain Tr- or Tn-UTR variant, respectively. A dualUTR consisting of a wild-type Tr- and a wild-type Tn-dualUTR DNA element, e.g. would be denoted as wtwt-dualUTR.

Generation and Screening of 5'-UTR Libraries Based on pAO-Tr and pAO-Tn

5'-UTR libraries were constructed in pAO-Tr and pAO-Tn by inserting the same annealed oligonucleotides (wild-type sequence and randomly doped synthetic oligonucleotide mixture) between their respective NdeI and PciI restriction sites for constructing the DI-UTR library. After transformation of *E. coli* DH5a, libraries with ~280,000 transformants (pAO-Tr-based) and ~370,000 transformants (pAO-Tn-based) were generated. Screening for high ampicillin tolerance was performed similar to Vee Aune et al. (2009, Microb. Biotechnol. 3: 38-47), only that 0.1 mM m-toluate in combination with 2, 3 or 4 g L$^{-1}$ ampicillin was used for screening the pAO-Tr-based 5'-UTR library and 0.5 mM m-toluate with 4, 5 or 6 g L$^{-1}$ ampicillin for screening the pAO-Tn-based 5'-UTR library. In the latter library, constructs with multiple insertions of the 5'-UTR oligonucleotides were observed, almost exclusively isolated from the strains tolerating the highest ampicillin concentrations. These were excluded from sequencing reactions by performing colony PCR using primer pair 5'-CCGGTAGCGGGA-CATGGG-3' (SEQ ID NO: 15) and 5'-CAAGGATCTTAC-CGCTGTTG-3' (SEQ ID NO: 16). The distinct classes of Pm 5'-UTR variants that were identified by screening the 5'-UTR libraries in pAO-Tr and pAO-Tn were denoted as Tr-UTRs or Tn-UTRs, respectively.

bla Expression Analysis

Ampicillin tolerance and β-lactamase enzyme activity are approximately proportional when bla is expressed from xylS/Pm in *E. coli*. Expression of bla was mainly assessed using ampicillin tolerance testing as described previously Vee Aune et al. (supra) due to the possibility to evaluate many strains in parallel using a 96-well format. For a few selected strains, however, an enzymatic assay was performed using the protocol described by Winther-Larsen et al. (2000 Metab. Eng. 2: 92-103). For some experiments, expression strain *E. coli* RV308 was used. Recombinant *E. coli* RV308 strains were grown in superbroth (3.2 g L L$^{-1}$ peptone, 2.0 g L$^{-1}$ yeast extract and 0.50 g L$^{-1}$ NaCl). Expression was induced in the mid-log phase and cultures were harvested 5 hours after induction with 2 mM m-toluate. 0.1 g pellet (wet weight) were washed with 0.9% NaCl and resuspended in 1.5 mL lysis buffer (25 mM Tris-HCl, pH 8.0, 100 mM NaCl, 2 mM EDTA) followed by incubation with 0.2 g L$^{-1}$ lysozyme on ice for 45 min and sonication (3 min, 35% duty cycle, 3 output control). After addition of 10 mM MgCl$_2$ and treatment with 125 U Benzonase® Nuclease (Sigma-Aldrich) for 10 min, the lysate was centrifuged to separate the soluble supernatant fraction from the pellet. The insoluble pellet fraction was resuspended in 1.5 mL lysis buffer. Both fractions were subjected to SDS-PAGE analysis using 12% ClearPage™ gels and ClearPAGE™ SDS-R Run buffer (C.B.S. Scientific) followed by staining with Coomassie Brilliant blue R-250 (Merck).

mCherry Production Analysis mCherry activity was determined with an Infinite M200 Pro multifunctional microplate reader (Tecan) by measuring the fluorescence of 200 μl untreated culture with excitation and emission wavelengths of 584 nm (9 nm bandwidth) and 620 nm (20 nm bandwidth), respectively, and normalization against OD$_{600}$. Measurements were performed in duplicates. Recombinant *E. coli* RV308 strains harbouring pDUTRc variants were grown in LB medium and induced with 2 mM m-toluate at OD$_{600}$=0.3-0.4. Recombinant *P. putida* KT2440 strains were grown in LB medium at 30° C. mCherry expression was induced with 2 mM m-toluate at OD$_{600}$=0.1-0.2 and cultures were harvested 5 hours after induction. SDS-PAGE analysis was performed as described above for strains producing β-lactamase.

Bioinformatics Tools

Translational initiation rates (TIRs) were determined using the reverse engineering function of the RBS calculator. The sequence input for this tools consisted of the 5'-UTR DNA sequence (up to 50 nt) and the first 50 nt of the bla or mcherry gene. 5'-UTRs with optimal translational features were generated applying the forward engineering function of the RBS calculator with the following constraints: First, only the DNA region covering the region randomized by the DI-library was changed. Secondly, flanking nucleotides at the 5'- and 3'-ends should be present so that insertion by PciI and NdeI (IB-UTR) or SacI and NdeI (Tn-dualUTR) was possible.

Example 1

Construction of Two Synthetic Operon Vectors for Identification of 5'-UTR Variants Specifically Stimulating Transcription or Translation The initial aim was to assess whether a screening method could be developed which would allow us to directly identify specific mutations within 5'-UTRs that lead to transcriptional or translational stimulation of gene expression. We therefore constructed two screening vectors called pAO-Tr and pAO-Tn which were designed to identify short length (as in wild-type Pm) 5'-UTR sequences that stimulate transcription or translation, respectively. This was achieved by integrating a slightly different synthetic bicistronic operon into each vector (FIGS. 1A and 1B). Common for both operons is the arrangement of celB (encoding phosphoglucomutase) as gene one and bla (encoding β-lactamase) as gene two. The celB gene was chosen as it can be very efficiently transcribed and translated and hence would not introduce any undesired restriction. Host tolerance to ampicillin correlates with the produced amounts of β-lactamase; making it easy to identify clones with the desired phenotype. Expression of celB and bla was driven by the positively regulated XylS/Pm regulator/promoter system, and both operons resided on a broad-host range mini-RK2 plasmid. The spacer region between the two genes in the operons ensured that translation of bla was only possible through de novo initiation (as opposed to translational read-through). This was confirmed by the elimination of the SD sequence upstream of bla abolishing expression of β-lactamase (results not shown).

A degenerated oligonucleotide 5'-UTR mixture was used to construct a 5'-UTR variant library (~280000 clones) in the pAO-Tr operon upstream of the first gene, celB. It was then assumed that any observed increased expression of bla (detected as higher host ampicillin tolerance) would be a consequence of increased transcription due to a new 5'-UTR variant. In the pAO-Tn operon, the same degenerated 5'-UTR oligonucleotide mixture was used for construction of a library (370000 clones) in which the oligonucleotides were inserted upstream of bla. By screening this library any observed increased ampicillin tolerance was assumed to be the result of increased de novo translation of bla as a consequence of a new 5'-UTR variant.

Example 2

Selection of Two Distinct Classes of 5'-UTR Variants by Screening of the pAO-Tr and pAO-Tn Libraries Recombinant E. coli strains harbouring the 5'-UTR libraries were plated on agar media containing m-toluate (induces transcription from Pm) and increasing ampicillin concentrations. From both libraries multiple colonies were isolated that showed elevated bla expression seemingly due to increased transcription (Tr-UTR variants) or as a consequence of improved translation (Tn-UTR variants) of the bla gene. Identified clones could grow at up to 2.5 g $L^{-1}$ ampicillin in the presence of a low (0.1 mM) inducer concentration. Plasmids were isolated from such clones and the regions corresponding to the 5'-UTR were sequenced. Synthetic oligonucleotides harbouring the identified Tr- or Tn-UTR mutations were then inserted into pAO-Tr and pAO-Tn to confirm that the initially observed ampicillin tolerance levels was actually caused by the UTR mutations. In total, the screening for increased bla expression resulted in identification of five Tr- and 21 Tn-UTRs (see Table 1), among which Tr-UTRs r31, r36, r50 (FIG. 2A), and Tn-UTRs n24, n44, n47, n58 (FIG. 2B) were selected for further characterization of their transcription- or translation-affecting properties. For comparison a previously characterized transcription enhancing Pm 5'-UTR variant, LV-2, was also included in this study.

TABLE 1

Sequences of 5'-UTR DNA sequences identified in different screening rounds of pAO-Tr- and pAO-Tn-based 5'-UTR libraries and resulting tolerated ampicillin concentrations of E. coli strains harbouring these 5'-UTR variants.

| Plasmid | SEQ ID NO: | Sequence 5'->3' | m-toluate concentration [-] | m-toluate concentration [0.1 mM] |
|---|---|---|---|---|
| pAO-Tr | 17 | AACATGT-ACAATAATAATGGAGTCATGAACATATG | 0.025 | 0.25 |
| LV-2 | 18 | ........-..C......CA......T.......... | 0.025 | 1.0 |
| SI-r11 | 19 | ........-..C........C.............. | 0.015 | 0.60 |
| SIII-r28 | 20 | ........-..-T.........AA............ | 0.015 | 0.80 |
| SIII-r31 | 21 | .......T..C..G..................... | 0.025 | 1.0 |
| SIII-r36 | 22 | ........-....GT.....C......A........ | 0.025 | 1.0 |
| SIII-r50 | 23 | .......T..........C..........T...... | 0.025 | 1.0 |
| pAO-Tn | 24 | AACATGTACAATAATAATGGAGTCATGAACATATG | 0.010 | 0.10 |
| SI-n2 | 25 | ........GTT.....-..........T........ | 0.25 | 2.0 |
| SI-n3 | 26 | ........T.A.C......AA.............. | 0.25 | 2.5 |
| SI-n13 | 27 | ........G...............C........ | 0.25 | 2.0 |
| SI-n15 | 28 | ...........C.....G.........T........ | 0.25 | 2.0 |
| SI-n16 | 29 | ...........C.............A........ | 0.25 | 1.5 |
| SI-n17 | 30 | ......G..................T........ | 0.25 | 2.0 |
| SI-n18 | 31 | ........A..A.G............T........ | 0.25 | 2.0 |
| SI-n24 | 32 | ..........T.....TA.........C........ | 0.25 | 2.0 |
| SII-n15 | 33 | ............C.....G......T........ | 0.25 | 1.5 |
| SII-n17 | 34 | ........A.C..............T........ | 0.25 | 2.0 |
| SII-n23 | 35 | .............G...........T........ | 0.25 | 2.0 |
| SII-n25 | 36 | .............G...........A........ | 0.25 | 1.0 |
| SII-n35 | 37 | ........A.......TA.......C........ | 0.25 | 1.5 |

TABLE 1 -continued

Sequences of 5'-UTR DNA sequences identified in different screening rounds of pAO-Tr- and pAO-Tn-based 5'-UTR libraries and resulting tolerated ampicillin concentrations of E. coli strains harbouring these 5'-UTR variants.

| Plasmid | SEQ ID NO: | Sequence 5'->3' | m-toluate concentration [-] | [0.1 mM] |
|---|---|---|---|---|
| SII-n39 | 38 | ........-.......____....T........ | 0.25 | 2.0 |
| SII-n41 | 39 | ........A..C..C...C____....T........ | 0.25 | 2.5 |
| SII-n42 | 40 | ........A.....CT..__.....A........ | 0.25 | 2.0 |
| SII-n44 | 41 | .......G......_A_.....C........ | 0.25 | 2.5 |
| SII-n47 | 42 | ........AT.A.C..__A_....T........ | 0.25 | 2.5 |
| SII-n48 | 43 | .........T...T....____AG..T........ | 0.25 | 2.0 |
| SII-n52 | 44 | ........GT...GA...____....T........ | 0.25 | 2.0 |
| SII-n58 | 45 | ..........T...C._A_........AT....... | 0.25 | 2.5 |
| SII-n59 | 46 | .........T..T.G.TA____....T........ | 0.25 | 2.5 |

The values depicted correspond to maximal ampicillin concentrations [g L$^{-1}$] at which growth was observed.
LV-2 is a previously identified Pm 5'-UTR variant.
SI, SII and SIII denote different rounds of screening.
No Tr-UTR variants could be identified in the second screening round.
Shine-Dalgarno sequences are underlined twice and the ATG start codon is written in boldface.

Initially, we wanted to investigate whether the identified Tr- and Tn-UTRs would solely cause transcriptional and translational stimulation, respectively. To study this we first inserted the Tr-UTRs in the Tn position (FIG. 2C), and Tn-UTRs in the Tr position (FIG. 2D) in the bicistronic operon. Ampicillin tolerance testing on agar media indicated that Tr-UTRs r31, r36, r50 in pAO-Tr caused an increase in b/a expression (relative to wild-type) also when inserted in the Tn position, and the same was observed for the previously identified transcription-stimulating LV-2 variant. These results were somewhat surprising, particularly since the LV-2 variant was previously found to stimulate bla transcript accumulation to nearly the same extent as the protein product β-lactamase. Furthermore, the LV-2 transcript displayed decay kinetics similar to that of the corresponding wild-type transcript. Together these results indicated that LV-2 is acting almost exclusively by stimulating transcription. Even though the explanation for the phenotypes of the Tr mutants in the Tn position are not clear these variant sequences were later found to be very useful for design of a new synthetic mRNA leader, i.e. a new type of UTR (see below).

For the Tn variants the phenotypes were more as expected. The observed stimulation of expression was highest for the variants n24, n44, n47 and n58 in pAO-Tn. As expected, Tn-UTRs inserted in front of celB did not yield an increase in ampicillin resistance indicating that they do not lead to increased transcription.

In addition to the phenotypic characterization, both Tr- and Tn-UTR DNA sequences were analyzed using the reverse engineering function of the RBS calculator. This tool determines a calculated translation initiation rate (TIR; see *Materials and Methods*) which reflects a theoretical approach to predict protein production levels. Based on this analysis Tr-UTRs exhibited a higher TIR (1.2-2.7 times) compared to that of the wild-type 5'-UTR. The TIR values for the Tn-UTRs were notably higher increasing the TIR of the wild-type 5'-UTR by a factor of 9.3-14.0 (Table 2), further supporting that the Tn-UTRs act on translation while the Tr-UTRs primarily, but perhaps not exclusively act at the level of transcription.

TABLE 2

Calculated translation initiation rates of Tr- and Tn-UTRs in combination with bla.

| UTR | TIR |
|---|---|
| wt | 522.82 |
| LV-2 | 2,371.77 |
| r31 | 716.42 |
| T36 | 625.94 |
| r50 | 1,407.17 |
| n24 | 4,872.99 |
| n44 | 7,306.38 |
| n47 | 5,331.95 |
| n58 | 7,306.38 |

Example 3

Design and Functionality Testing of a New and Extended Length 5'-UTR (i.e. Synthetic mRNA Leader) Containing Both Tr and Tn Variant Sequences We hypothesized that a longer 5'-UTR might act much more stimulatory than each of its two units separately. In this design we also inserted a spacer region to physically separate the Tr and Tn units, allowing modularity and flexibility for later modifications (FIG. 3). The new UTR (here termed dualUTR or a synthetic mRNA leader) was inserted into the XylS/Pm regulator/promoter system and mini-RK2 replicon (but no synthetic operon) as described above. Twenty-five dualUTR constructs were created by combining Tr-UTRs (one wild-type and four variants) at the 5'-end (Tr-position) and the same for Tn-UTRs at the 3'-end (Tn-position) (FIG. 3). Recombinant *E. coli* strains harbouring plasmids with each of these 25 TrTn-dualUTRs were initially subjected to ampicillin tolerance testing. Among the combinations with varying Tr units and wild-type Tn unit r31 wt caused the strongest enhancement of ampicillin tolerance (3.3-fold compared to the wtwt construct) (FIG. 3). Strains harbouring the four wtTn combinations tolerated four- (wtn58) to 32-times (wtn24) more ampicillin than strains with the reference wtwt construct. Interestingly, mutations found in the two Tr-UTR DNA elements, r31 and r50, exerted a stimulatory effect on top of the effect caused by the mutations of the Tn-UTR DNA elements alone. All r31Tn combinations surpassed the stimulatory effects of all the wtTn combinations, and the same was true for three out of the four r50Tn combinations. The Tn-UTR n47 exhibited a stimulatory phenotype in almost all combinations tested (except r36n47), and generally the enhancement of bla expression was also stronger than the sum of expression enhancement achieved by the individual Tr- and Tn-UTRs.

The initial characterizations described demonstrated that it was feasible to generate strongly improved 5'-UTR sequences by fusing primarily transcription and translation stimulating sequences in a single 5'-UTR. It was also encouraging that this could be shown by only using a small number of Tr- and Tn-UTR variants, meaning that successful combinations can be predicted to occur with high frequency.

Example 4

Characterization of the Newly Designed dualUTR Sequences at the Transcript and Protein Production Level Samples collected from *E. coli* strains with four dualUTR constructs, wtwt, r31 wt, wtn47, and r31n47 were subjected to relative quantitative real-time reverse-transcription PCR (qPCR) and β-lactamase enzymatic activity assays. The results confirmed that r31 and n47 indeed exhibited transcription and translation stimulating characteristics, respectively (FIG. 4A). The r31 wt UTR variant stimulated transcription 2.7-fold while β-lactamase activity increased only 1.7-fold. In contrast, the wtn47 dualUTR exhibited a strong translation stimulating phenotype, resulting in a 42-fold increased β-lactamase enzyme activity compared to a 10-fold increase in accumulated bla transcript relative to the wtwt dualUTR. It may well be that the transcript stimulation in this case is caused by ribosome protection of mRNA from degradation due to the very efficient translation. Interestingly, the r31n47 combination caused an enhancement of both processes leading to an extremely strong stimulation of expression (46- and 170-fold at the transcript and protein levels, respectively). This effect was more than the multiplicity of the relative effects the single Tr- and Tn-UTR elements had on their own.

The bla gene is generally expressed at low levels per gene copy, explaining how a 170-fold stimulation is possible. In addition a low copy-number plasmid (four-seven copies per chromosome) was used in the experiments reported here. However, the very strong stimulation observed with r31n47 suggested to us that the produced β-lactamase might in this case be sufficient to be directly visualized with SDS-PAGE. Total cellular protein produced in four selected (plus negative control) bla-expressing strains was separated into the soluble and insoluble fraction and analyzed on an SDS-PAGE. β-lactamase could be visualized in the soluble fraction of sonicated cell lysates from strains harbouring constructs with the wtn47- and r31n47 UTRs, and also in the insoluble fraction from the r31n47 construct (FIG. 4B upper panel). Specific detection of β-lactamase was also performed by Western blotting and the signal strengths generally correlated with the protein activities (FIG. 4B lower panel).

Example 5

Assessment of the Functionality of the dualUTR Design Using a Different Reporter Gene As the Tn-UTR variants used in the bifunctional were identified by screening for high bla expression, it was also of interest to analyze to what extent the stimulation was gene-specific. To assess this potential context dependency, bla was substituted by mCherry, encoding a red fluorescent protein. Production of this protein was analyzed with plasmid constructs containing the wtwt, r31 wt, wtn47 and r31n47 dualUTR variants, using a fluorimetric assay and direct protein gel analysis. The fluorescence data confirmed that the combination of the transcription stimulating r31 and the translation stimulating n47 led to strong synergistic effects on protein production also for mCherry, although the effects were somewhat weaker than for β-lactamase (FIG. 5A). Correspondingly, the mCherry protein could be easily visualized directly by SDS-PAGE both in the soluble and insoluble fraction, particularly from r31n47 (FIG. 5B). Stimulation of mCherry expression by the r31n47 dualUTR went far beyond that of the variants r31 and n47 alone, thereby confirming the corresponding observation for bla. These results clearly demonstrate that there is a very significant potential in 5'-UTR design for the improvement of recombinant gene expression.

Example 6

Use of a Rational Design Tool to Adapt the dualUTR to Different Coding Regions

The results described above showed that combination of mutations that primarily stimulate transcription or translation within the dualUTR gave very good expression outcomes for at least the two tested genes, bla and mCherry. It is desirable to be able to predict theoretically the potential Tn-UTR interactions with coding sequences. For example, some 5' proximal coding sequences may sequester the SD sequence causing inefficient translation initiation. Therefore we applied a widely used RBS design tool, the RBS calculator, to design Tn-UTRs that are adapted to avoid undesired interactions with the 5' proximal end of the coding sequence. The bla and mCherry genes were again used as reporters to enable comparisons with the sequences identified by experimental screening. In total, six such designed Tn-UTRs were synthesized: three for the bla coding region and three for mCherry (named, dTn-UTRs, Table 3). The predicted TIR values were 60-80-fold higher compared to n47-b/a, and 50-70-fold higher compared to n47-mcherry (Table 4). All six dTn-UTRs were inserted into the dualUTR construct with either the wt- or the r31-variant in the Tr-position. A direct experimental comparison with n47, the best sequence from screening, revealed that, for bla, all three dTn-UTRs stimulated expression to an extent that was not very different from that of n47. Also, the r31-dTn1 UTR is at least as good as r31n47 (FIG. 6A). Similar observations were also be made for mCherry (FIG. 6B). Tr-UTR r31 in combination with the designed Tn-UTRs led to 9 (dTn4), 46 (dTn5) and 46 (dTn6) times relative increase vs. 58 times with the Tn-UTR n47. These results show that the RBS calculator can be applied predictably to enhance production of a protein, provided the UTR design described here is applied.

To strengthen our observation that physical separation of the mutations within a 5'-UTR leading to increased transcription or translation, respectively, are necessary to improve reliability of rational design tools, we utilized the RBS calculator to design three Pm 5'-UTR variants (32 nt in length) with maximized TIR that were specific for the bla gene (dlB1-3; Table 3). When we tested the effect of these designed 5'-UTR variants on bla expression, it became evident that optimizing a short 5'-UTR for maximum TIR only is not sufficient to maximize protein production (FIG. 7). Recombinant *E. coli* DH5α strains harbouring constructs with the LV-2 Pm 5'-UTR variant for instance tolerated more than 13 g L$^{-1}$ ampicillin while strains with the best designed 5'-UTR variant (dIB2) only tolerated a maximum of 8 g L L$^{-1}$ ampicillin.

The dualUTR design is superior to the previously short optimized 5'-UTRs mainly due to two factors: (i) Higher expression levels can be achieved with the extended length UTRs than with the improved short 5'-UTRs alone; (ii) Due to separation of the transcription and translation influencing regions, a Tn-UTR region can be improved solely based on its translation influencing characteristics, which means that sequences can be optimized in silico.

TABLE 3

Sequences of various 5'-UTR DNA sequences.

| Name | Sequence 5'->3' |
|---|---|
| dIB1 | AACATGTTCGTCTTCACGC<u>TAAGGAGGT</u>ACATATG (SEQ ID NO: 47) |
| dIB2 | AACATGTTACTTATACG<u>AGGAGGT</u>TACAGCATATG (SEQ ID NO: 48) |
| dIB3 | AACATGTACCGTTCTTTCTAAGC<u>GAGGT</u>TCATATG (SEQ ID NO: 49) |
| dTn1 | <u>GAGCTC</u>CATTATTATTGTATATGTGCATCAATTAC TA<u>AGGAGGT</u>ATACTATG (SEQ ID NO: 50) |
| dTn2 | <u>GAGCTC</u>CATTATTATTGTATATGTGCATCACCCTT TA<u>AGGAGGT</u>TTACTATG (SEQ ID NO: 51) |
| dTn3 | <u>GAGCTC</u>CATTATTATTGTATATGTACCGTACCCGT TA<u>AGGAGGT</u>TTTCTATG (SEQ ID NO: 52) |
| dTn4 | <u>GAGCTC</u>CATTATTATTGTATATGTAACAAGGCAGA ATA<u>AGGAGGT</u>TCATATG (SEQ ID NO: 53) |
| dTn5 | <u>GAGCTC</u>CATTATTATTGTATATGTGGATATACCCA GTA<u>AGGAGGT</u>ACATATG (SEQ ID NO: 54) |
| dTn6 | <u>GAGCTC</u>CATTATTATTGTATATGTATATAAGGATT AG<u>AGGAGGT</u>AATATATG (SEQ ID NO: 55) |

Shine-Dalgarno sequences are double-underlined and the ATG start codon is written in boldface.
dIB1-3 are sequences with the same length as the Pm 5'-UTR that were designed by the RBS calculator to yield the highest translation initiation rate possible for expression of bla.
dTn1-6 represent sequences of six Tn-UTR dualUTR elements with maximal TIRs for bla (dTn 1-3) or mcherry (dTn 4-6).

TABLE 4

Calculated translation initiation rates of Tn-dualUTR DNA elements in combination with bla and mcherry. dTn1-6 represent sequences of six Tn-UTR dualUTR elements with maximal TIRs for bla (dTn 1-3) or mcherry (dTn 4-6).

| | TIR | |
|---|---|---|
| Tn-dualUTR | bla | mcherry |
| wt | 598.4 | 2,308.6 |
| n24 | 5,332.0 | 5,678.7 |
| n44 | 7,994.5 | 25,075.0 |
| n47 | 5,834.1 | 12,766.2 |
| n58 | 3,461.4 | 4,743.2 |

TABLE 4-continued

Calculated translation initiation rates of Tn-dualUTR DNA elements in combination with bla and mcherry. dTn1-6 represent sequences of six Tn-UTR dualUTR elements with maximal TIRs for bla (dTn 1-3) or mcherry (dTn 4-6).

| | TIR | |
|---|---|---|
| Tn-dualUTR | bla | mcherry |
| dTn1/dTn4 | 349,161.5 | 856,820.0 |
| dTn2/dTn5 | 418,029.8 | 819,114.1 |
| dTn3/dTn6 | 478,456.9 | 655,630.7 |

Example 7

Assessment of the Functionality of the Bifunctional UTR Concept in an Alternative Host One of the great advantages of mini-RK2 replicons and the XylS/Pm system is that they both function in Gram-negative hosts other than E. coli. One such host, Pseudomonas putida shares the same anti-SD sequence within the 16S rRNA with E. coli. We therefore hypothesized that the dualUTR constructs might also display similar effects on recombinant protein production as observed in E. coli. Constructs with the TrTn dualUTR combinations wtwt, r31 wt, wtn47 and r31n47 and the mCherry reporter gene were transferred to P. putida KT2440 (strain cured for the RK2 plasmid) and mCherry production was analyzed (FIG. 8A). A strong synergistic effect of combining the r31 Tr-UTR DNA element with the n47 Tn-UTR DNA element was also observed in P. putida KT2440, even though r31 alone had a somewhat negative effect on expression. In addition, mCherry production appeared to be more effective in this host compared to E. coli judged by the stronger bands on the SDS-PAGE gel (FIG. 8B). The reduction of mCherry production seen for the r31 wt-compared to the wtwt UTR may potentially be attributed to a less optimal context between the Pm promoter and the r31 UTR DNA sequence in this host. In any case, the data collected in P. putida support the hypothesis that physical separation of the transcription- and translation-stimulating elements leads to a far better improvement of protein production than achieved by identifying mutations that simultaneously influence both processes. It also means that the principle is not restricted to any particular bacterial host.

CONCLUSIONS

This study shows that mutations within 5'-UTRs that primarily stimulate transcription or translation can be identified by library screening. By then physically separating these mutations within a re-designed 5'-UTR DNA region with extended length, we surprisingly demonstrated that a strongly improved expression output can be achieved. The applicability of already existing RBS design tools was also significantly improved by this strategy, as poorly understood negative effects on transcription can be avoided. The identification of 5'-UTR DNA elements specifically enhancing transcription and the synergistic effect of this element together with the effect of a translation-enhancing a 5'-UTR DNA on protein production was unexpected. However, there can be a reasonable expectation, based on the results disclosed herein, that the synthetic mRNA leaders can be applied to a wider range of genes than the two tested here. Accordingly, the present invention is universally applicable to improve recombinant expression, particularly in bacteria.

The invention claimed is:

1. A method of enhancing expression of a desired gene product in a recombinant gene expression system, said method comprising expressing said gene using a synthetic mRNA leader which comprises from 5' to 3':
   (i) a first mRNA leader sequence element;
   (ii) a spacer region; and
   (iii) a second mRNA leader sequence element;
   wherein said first mRNA leader sequence element is a first mutated Pm mRNA leader capable of enhancing transcription of a gene relative to an unmutated Pm mRNA leader sequence of SEQ ID NO:1, wherein the first mutated Pm mRNA leader has at least 80% sequence identity to the unmutated Pm mRNA leader sequence of SEQ ID NO:1; and
   wherein said second mRNA leader sequence element is a second mutated Pm mRNA leader capable of enhancing the translation of a gene transcript relative to an unmutated Pm mRNA leader sequence of SEQ ID NO:1, wherein the second mutated Pm mRNA leader has at least 80% sequence identity to the unmutated Pm mRNA leader sequence of SEQ ID NO:1.

2. The method of claim 1, wherein each mutated Pm mRNA leader sequence is generated by introducing one or more mutations into the DNA corresponding to the unmutated Pm mRNA leader of SEQ ID NO:1, and selecting an mRNA leader mutant which enhances transcription of a gene and/or translation of a gene transcript.

3. The method of claim 1, wherein said spacer region comprises 4-200 nucleotides.

4. The method of claim 1, wherein said recombinant gene expression system comprises a promoter selected from any one of a Pm promoter, a Ptac promoter, a PtrcT7 RNA polymerase promoter, $\lambda P_L$ or a $P_{BAD}$ promoter.

5. The method of claim 1, wherein each mutated Pm mRNA leader comprises 1 to 6 mutations.

6. The method of claim 2, wherein in said second mutated Pm mRNA leader said one or more mutations are present at or downstream of position +8 from the transcriptional start site.

7. The method of claim 2, wherein in said second mutated Pm mRNA leader said one or more mutations are not made to the Shine-Dalgarno sequence.

8. The method of claim 2, wherein in said second mutated Pm mRNA leader said one or more mutations do not include the insertion or creation of functional AU-rich sites.

9. The method of claim 1, wherein a vector comprising a promoter, a DNA region corresponding to said synthetic mRNA leader and said gene encoding said desired gene product is introduced into a host cell and said host cell is cultured to allow said gene to be expressed.

10. The method of claim 2, wherein said mutations are selected from a substitution, a deletion or an addition, or a combination thereof.

11. The method of claim 4, wherein said promoter is a Pm promoter.

12. The method of claim 9, wherein said host cell is a prokaryotic cell.

13. The method of claim 9, wherein said method further comprises a step of recovering, purifying, extracting or isolating the gene product expressed by said host cell.

14. The method of claim 1, wherein the first mutated Pm mRNA leader is selected from any one of SEQ ID NOs: 18-23 and/or said second mutated Pm mRNA leader is selected from any one of SEQ ID NOs: 25-46.

15. The method of claim 1, wherein the first mutated Pm mRNA leader is selected from any one of SEQ ID NOs: 21-23 and/or said second mutated Pm mRNA leader is selected from any one of SEQ ID NOs: 32, 41, 42 and 45.

16. The method of claim 1, wherein the first mutated Pm mRNA leader is SEQ ID NO: 21 and said second mRNA leader is SEQ ID NO: 42.

* * * * *